United States Patent [19]

Martens et al.

[11] Patent Number: 4,758,511

[45] Date of Patent: Jul. 19, 1988

[54] CDNA CLONES CODING FOR POLYPEPTIDES EXHIBITING IGE BINDING FACTOR ACTIVITY

[75] Inventors: Christine L. Martens, Menlo Park; Kevin W. Moore, San Bruno, both of Calif.; Kimishige Ishizaka, Towson; Thomas F. Huff, Baltimore, both of Md.

[73] Assignees: DNAX Research Institute of Molecular and Cellular Biology, Inc., Palo Alto, Calif.; The Johns Hopkins University, Baltimore, Md.

[21] Appl. No.: 590,430

[22] Filed: Mar. 16, 1984

[51] Int. Cl.$^4$ .................. C12P 21/00; C12P 21/02; C12N 15/00; C12N 5/00; C12N 1/00; C07H 17/00
[52] U.S. Cl. .................. 435/68; 435/240.2; 435/320; 435/172.3; 435/70; 536/27; 935/11; 935/32; 935/70
[58] Field of Search .............. 435/68, 240, 241, 253, 435/255, 172.3, 320; 536/27; 935/11, 13, 32, 70, 49

[56] References Cited

PUBLICATIONS

Huff, T. et al, *J. Immunol.*, vol. 129, No. 2, pp. 509–514, 1982.
Martens, C. et al., *Proc. Natl. Acad. Sci.*, vol. 82, pp. 2460–2464, 1985.
Okayama, H. et al., *Molec. and Cell Biol.*, vol. 3, No. 2, pp. 280–289, 1983.
Elder, J. T. et al., *Ann. Rev. Genet.*, vol. 15, pp. 295–340, 1981.
Moriarty, A. et al., *Proc. Natl. Acad. Sci.*, vol. 78, No. 4, pp. 2606–2610, 1981.

*Primary Examiner*—Thomas G. Wiseman
*Assistant Examiner*—Jayme A. Huleatt
*Attorney, Agent, or Firm*—William M. Smith; Stephen C. Macevicz

[57] ABSTRACT

Plasmid vectors are provided that carry complementary DNA (cDNA) clones coding for polypeptides exhibiting mammalian IgE binding factor activity. One of these clones contains an open reading frame consisting of 556 codons. The cDNA is derived from messenger RNA isolated from a rat/mouse T-cell hybridoma line. The cDNA was cloned by incorporation into a pcD plasmid vector. The plasmid vector also contains DNA segments from the SV40 virus, permitting expression of the cDNA to form a polypeptide having IgE potentiating activity after transfection into a mammalian host cell, such as monkey Cos7 cells.

16 Claims, 8 Drawing Sheets

```
               10          20          30          40          50
         GCTAGAGTAC  CAGTGAGTAC  AGCTTTACGA  GGTAAGTCTG  ATCTTGAACT 60          70          80          90
         TTCTAAGGAA  ATTCAAGACA  GTCTATCAGA  AGTAAAGTGG  AAA ATG GCT TTA
                                                            MET Ala Leu 108                     123                     138
         CAA GTT ATG TTT GGC CTT GAA TTT TTT CTA GTG TTA GAA GCC CTT TTG
         Gln Val MET Phe Gly Leu Glu Phe Phe Leu Val Leu Glu Ala Leu Leu 153                     168                     183         198
         TTC CTT TTC ACA TGT TAT CAA GTG GTT AAG GCA GGG CGG ATT CTA GAT
         Phe Leu Phe Thr Cys Tyr Gln Val Val Lys Ala Gly Arg Ile Leu Asp 213                     228             243
         GAA ATT CAG GAC AAG CTA TCA GAA GTA AAG CGG GGA GAG AGA GTA GGA
         Glu Ile Gln Asp Lys Leu Ser Glu Val Lys Arg Gly Glu Arg Val Gly 258                     273                 288
         ACA AAG AGG AAA TAT GGT ACA CAA AAT AAG TAT ACA GGC CTT TCC AAG
         Thr Lys Arg Lys Tyr Gly Thr Gln Asn Lys Tyr Thr Gly Leu Ser Lys 303                     318                 333
         GGT CTT GAA CCC GAG GAA AAG TTA AGG TTA GGT AGG AAT ACC TGG AGA
         Gly Leu Glu Pro Glu Glu Lys Leu Arg Leu Gly Arg Asn Thr Trp Arg 348                     363                 378
         GAG ATT AGA AGA AAA AGA GGA AAA AGG GAA AAG AAG AAA GAT CAA TTA
         Glu Ile Arg Arg Lys Arg Gly Lys Arg Glu Lys Lys Lys Asp Gln Leu 393                 408                     423                 438
         GCG GAG GTC TCT AGG AAA AGG AGC CTG TGC TCA TCG CTG GAT GGG CTC
         Ala Glu Val Ser Arg Lys Arg Ser Leu Cys Ser Ser Leu Asp Gly Leu 453                     468                 483
         GGG AAG CCA GCT CTT AGT AGC TCT GAA GCA GGT GAA GAA TCC TCC TCT
         Gly Lys Pro Ala Leu Ser Ser Ser Glu Ala Gly Glu Glu Ser Ser Ser 498                     513                 528
         GAG GAA ACA GAC TGG GAG GAA GAA GCA GCC CAT TAC CAG CCA GCT AAT
         Glu Glu Thr Asp Trp Glu Glu Glu Ala Ala His Tyr Gln Pro Ala Asn
```

FIG. 1

```
      543                    558                     573
TGG TCA AGA AAA AAG CCA AAA GCG GCT GGC GAA GGC CAG TTT GCT GAT
Trp Ser Arg Lys Lys Pro Lys Ala Ala Gly Glu Gly Gln Phe Ala Asp 588                    603                     618
TGG CCT CAG GGC AGT CGG CTT CAA GGT CCG CCC TAT GCG GAG TCC CCG
Trp Pro Gln Gly Ser Arg Leu Gln Gly Pro Pro Tyr Ala Glu Ser Pro 633                 648                    663                678
CCC TGC GTA GTG CGT CAG CAA TGC GCA GAG AGA TGC GCA GAG AGG CAG
Pro Cys Val Val Arg Gln Gln Cys Ala Glu Arg Cys Ala Glu Arg Gln 693                    708                    723
TGC GCA GAG AGG CAG TGC GCA GAC TCA TTC ATT CCC AGA GAG GAA CAA
Cys Ala Glu Arg Gln Cys Ala Asp Ser Phe Ile Pro Arg Glu Glu Gln 738                    753                    768
AGG AAA ATA CAA CAG GCA TTT CCG GTC TTT GAA GGA GCC GAG GGT GGG
Arg Lys Ile Gln Gln Ala Phe Pro Val Phe Glu Gly Ala Glu Gly Gly 783                    798                    813
CGT GTC CAC GCT CCG GTA GAA TAC TTA CAA ATT AAA GAA ATT GCC GAG
Arg Val His Ala Pro Val Glu Tyr Leu Gln Ile Lys Glu Ile Ala Glu 828                    843                    858
TCG GTT CGT AAA TAT GGA ACC AAT GCT AAT TTT ACC TTG GTG CAG TTA
Ser Val Arg Lys Tyr Gly Thr Asn Ala Asn Phe Thr Leu Val Gln Leu 873                    888                    903                918
GAC AGG CTC GCC GGC ATG GCA CTA ACT CCT GCT GAC TGG CAA ACG GTT
Asp Arg Leu Ala Gly MET Ala Leu Thr Pro Ala Asp Trp Gln Thr Val 933                    948                    963
GTA AAA GCC GCT CTC CCT AGT ATG GGC AAA TAT ATG GAA TGG AGA GCG
Val Lys Ala Ala Leu Pro Ser MET Gly Lys Tyr MET Glu Trp Arg Ala 978                    993                    1008
CTT TGG CAC GAA GCT GCA CAA GCG CAG GCC CGA GCA AAC GCA GCT GCT
Leu Trp His Glu Ala Ala Gln Ala Gln Ala Arg Ala Asn Ala Ala Ala
```

FIG.1

```
              1023                    1038                    1053
TTG ACT CCA GAG CAG AGA GAT TGG ACT TTT GAC TTG TTA ACG GGT CAG
Leu Thr Pro Glu Gln Arg Asp Trp Thr Phe Asp Leu Leu Thr Gly Gln 1068                    1083                    1098
GGA GCT TAT TCT GCT GAT CAG ACA AAC TAC CAT TGG GGA GCT TAT GCC
Gly Ala Tyr Ser Ala Asp Gln Thr Asn Tyr His Trp Gly Ala Tyr Ala 1113                    1128                    1143               1158
CAG ATT TCT TCC ACG GCT ATT AGG CCT GGA AGG CGC TCT CGA GCA GGT
Gln Ile Ser Ser Thr Ala Ile Arg Pro Gly Arg Arg Ser Arg Ala Gly 1173                    1188                    1203
GAA ACC ACT GGT CAG TTA ACA AAG ATA ATC CAG GGA CCT CAG GAA TCC
Glu Thr Thr Gly Gln Leu Thr Lys Ile Ile Gln Gly Pro Gln Glu Ser 1218                    1233                    1248
TTC TCA GAT TTT GTG GCC AGA ATG ACA GAG GCA GCA GAG CGT ATT TTT
Phe Ser Asp Phe Val Ala Arg MET Thr Glu Ala Ala Glu Arg Ile Phe 1263                    1278                    1293
GGA GAG TCA GAG CAA GCT GCG CCT CTG ATA GAA CAG CTA ATC TAT GAG
Gly Glu Ser Glu Gln Ala Ala Pro Leu Ile Glu Gln Leu Ile Tyr Glu 1308                    1323                    1338
CAA GCC ACA AAG GAG TGC CGA GCG GTC CAT AGC CCC AAG AAA GAA CAA
Gln Ala Thr Lys Glu Cys Arg Ala Val His Ser Pro Lys Lys Glu Gln 1353                    1368                    1383               1398
AGG CTT ACA AGA CTG GCT CAG GGT CTG TCG AGA GCT TGG GGG AAA CCC
Arg Leu Thr Arg Leu Ala Gln Gly Leu Ser Arg Ala Trp Gly Lys Pro 1413                    1428                    1443
AGA CTC CTT AAG ACT GAT AAT GGA CCA GCT TAT ACG TCT CAA AAA TTC
Arg Leu Leu Lys Thr Asp Asn Gly Pro Ala Tyr Thr Ser Gln Lys Phe 1458                    1473                    1488
CAA CAG TTC TGC CGT CAG ATG GAC GTG ACC CAC CTG ACT GGA CTT CCA
Gln Gln Phe Cys Arg Gln MET Asp Val Thr His Leu Thr Gly Leu Pro
```

FIG. 1

```
                    1503                    1518                    1533
TAC AAC CCT CAA GGA CAG GGT ATT GTT GAG CGT GCG CAT CGC ACC CTC
Tyr Asn Pro Gln Gly Gln Gly Ile Val Glu Arg Ala His Arg Thr Leu
                    1548                    1563                    1578
AAA GCC TAT CTT ATA AAA CAG AAG AGG GGA ACT TTT GAG GAG ACT GTA
Lys Ala Tyr Leu Ile Lys Gln Lys Arg Gly Thr Phe Glu Glu Thr Val
1593                    1608                    1623                    1638
CCC CGA GCA CCA AGA GTG TCG GTG TCT TTG GCA CTC TTT ACA CTC AAT
Pro Arg Ala Pro Arg Val Ser Val Ser Leu Ala Leu Phe Thr Leu Asn
                    1653                    1668                    1683
TTT TTA AAT ATT GAT GCT CAT GGC CAT ACT GCG GCT GAA CGT CAT GTT
Phe Leu Asn Ile Asp Ala His Gly His Thr Ala Ala Glu Arg His Val
                    1698                    1713                    1728
CAG AGC CAG ATA GGC CCA ATG AGA TGG TTA AAT GGA AAA ATG TCC TTG
Gln Ser Gln Ile Gly Pro MET Arg Trp Leu Asn Gly Lys MET Ser Leu
                    1743                    1758                    1780
ATA ATA AAT GGT ATG GCC CGG ATC CTA TCT TGA TAA GATCCAGGGG
Ile Ile Asn Gly MET Ala Arg Ile Leu Ser  *   *
            1790        1800        1810        1820        1830
         AGCTATCTGT  GTTTCCCCAC  AGAATGAAGA  CAACCCATTT  TGGGTACCAG
            1840        1850        1860        1870        1880
         AAAGACTCAC  CCGAAAAATC  CAGACTGACC  AAGGGAATAC  TAATGTCCCT 1890        1900        1910        1920        1930
         CGTCTTGGTG  ATGTCCAGGG  CGTCAATAAT  AAAGAGAGAG  CAGCGTTGGG
            1940        1950        1960        1970        1980
         GGATAATGTC  GACATTTCCA  CTCCCAATGA  CGGTGATGTA  TAATGCTCAA
            1990        2000        2010        2020        2030
         GTATTCTCCT  GCTTTTTTAC  CACTAACTAG  GAACTGGGTT  TAGCCTTGAT
            2040        2050        2060        2070        2080
         TCAGACAGCC  TTGGCTCTGT  CTGGACAGGT  CCAGATGACT  GACACCATTA
```

FIG. 1

|  |  |  |  |  |
|---|---|---|---|---|
| 2090 | 2100 | 2110 | 2120 | 2130 |
| ACACTTTGTC | AGCCTCAGTG | ACTACAGTCA | TAGATGAACA | GGCCTCAGCT |
| 2140 | 2150 | 2160 | 2170 | 2180 |
| AATGTCAAGA | TACAGAGAGG | TCTCATGCTG | GTTAATCAAC | TCATAGATCT |
| 2190 | 2200 | 2210 | 2220 | 2230 |
| TGTCCAGATA | CAACTAGATG | TATTATGACA | AATAACTCAG | CAGGGATGTG |
| 2240 | 2250 | 2260 | 2270 | 2280 |
| AACAAAAGTT | TCCGGGATTG | TGTGTTATTT | CCATTCAGTA | TGTTAAATTT |
| 2290 | 2300 | 2310 | 2320 | 2330 |
| ACTAGGGCAG | CTAATTTGTC | AAAAAGTCTT | TTTCAGTATA | TGTTACAGAA |
| 2340 | 2350 | 2360 | 2370 | 2380 |
| TTGGATGGCT | GAATTTGAAC | AGACCCTTCG | AGGCTTGCCA | TCATTCAGGT |
| 2390 | 2400 | 2410 | 2420 | 2430 |
| CAACTCCACG | CGCTTGGACC | TGTCCCTGAC | CAAAGGATTA | CCCAATTGGA |
| 2440 | 2450 | 2460 | 2470 | 2480 |
| TCTCCTCAGC | ATTTTCTTTC | TTTAAAAAAT | GGGTGGGATT | AATATTATTT |
| 2490 | 2500 | 2510 | 2520 | 2530 |
| GGAGATACAC | TTTGCTGTGG | ATTAGTGTTG | CTTCTTTGAT | TGGTCTGTAA |
| 2540 | 2550 | 2560 | 2570 | 2580 |
| GCTTAAGGCC | TAAACTAGGA | GAGACAAGGT | GGTTATTGCC | CAGGCGCTTG |
| 2590 | 2600 | 2610 | 2620 | 2630 |
| CAGGACTAGA | ACATGGAGCT | TCCCCTGATA | TATCTATGCT | TAGGCAATAG |
| 2640 | 2650 | 2660 | 2670 | 2680 |
| GTCGCTGGCC | ACTCAGCTCT | TATATCTCAC | GAGGCTAGTC | TCATTGCACG |
| 2690 | 2700 | 2710 | 2720 | 2730 |
| GGATAGAGTG | AGTGTGCTTC | AGCAGCCCGA | GAGAGTTGCA | AGGCTAAGCA |
| 2740 | 2750 | 2760 | 2770 | 2780 |
| CTGCAATGGA | AAGGCTCTGC | GGCATATATG | AGCCTATTCT | AGGGAAACAT |
| 2790 | 2800 | 2810 | 2820 | 2830 |
| GTCATCTTTC | ATGAAGGTTC | AGTGTCCTAG | TTCCCTTCCC | CCAGGCAAAA |
| 2840 | 2850 | 2860 | 2870 | 2880 |
| CGACACGGGA | GCAGGTCAGG | GTTGCTCTGG | GTAAAAGCCT | GTAAGCCTAA |

FIG. 1

```
     2890       2900       2910       2920       2930
GAGCTAATCC TGTACATGGC TCCTTTACCT ACACACTGGG GATTTGACCT
     2940       2950       2960       2970       2980
CTATCTCCAC TCTCATTAAT ATGGGTGGCC TATTTGCTCT TATTAAAAGA
     2990       3000       3010       3020       3030
AAAAGGGGGA GATGTTGGGA GCCGCCCCCA CATTCGCCGT TACAAGATGG
     3040       3050       3060       3070       3080
CGCTGACATC CTGTGTTCTA AGTGGTAAAC AAATAATCTG CGCATGTGCC
     3090       3100       3110       3120       3130
AAGGGTATCT TATGACTACT TGTGCTCTGC CTTCCCCGTG ACGTCAACTC
     3140       3150       3160       3170       3180
GGCCGATGGG CTGCAGCCAA TCAAGGAGTG ATACGTCCGA GGCGAAGGAG
     3190       3200       3210       3220       3230
AATGCTCCTT AAGAGGGACG GGGTTTTCGT TTTCTCTCTC TCTTGCTTCT
     3240       3250       3260       3270       3280
TGCTCTCTTG CTTCTTGCTC TCTTGCTTCC TGCACCCTGG CTCCTGAAGA
     3290       3300       3310       3320       3330
TGTAAGAAAT AAAGCTTTGC -GCAGAAAAA AAAAAAAAAA AAAAAAAAAA
     3340       3350       3360       3370
AAAAAAAAAA AAAAAAGTAC CTTCTGAGGC GGAAAGAA-C AGCG
```

FIG. 1

CDNA CLONES CODING FOR POLYPEPTIDES EXHIBITING IGE BINDING FACTOR ACTIVITY

FIELD OF THE INVENTION

This invention relates generally to the application of recombinant DNA technology to elucidate the control mechanisms of the mammalian immune response, and more particularly, to the isolation of cDNA clones coding for polypeptides exhibiting immunoglobulin-binding factor activity.

BACKGROUND OF THE INVENTION

Recombinant DNA technology refers generally to the technique of integrating genetic information from a donor source into vectors for subsequent processing. This typically entails introducing exogenous DNA into a host, whereby the transferred genetic information is copied and/or expressed in the new environment. Commonly, the genetic information exists in the form of complementary DNA (cDNA) derived from messenger RNA (mRNA) coding for a directed protein product. The vector is frequently a plasmid having the capacity to incorporate cDNA for subsequent replication in a host and, in some cases, actually to control expression of the cDNA and direct the host to make the encoded product.

This technology has progressed extremely rapidly in recent years, and a variety of exogenous proteins has been expressed in a variety of hosts. By way of example, some of the eukaryotic proteins to produced include: proinsulin (Naber, S. et al., Gene 21: 95–104 [1983]); interferons (Simon, L. et al., Proc. Nat. Acad. Sci. U.S.A., 80: 2059–2062 [1983] and Derynck, R. et al., Nucl. Acids Res. 1: 1819–1837 [1983]); and growth hormone (Goeddel, D., et al, Nature 281: 544–548 [1979]). (These publications and other herein referenced materials have been included to provide additional details on the background of the pertinent art and, in particular instances, the practice of invention, and are all incorporated herein by reference.)

It is now generally accepted that the mammalian immune response is mediated by a series of complex cellular interactions, coined the "immune network". The immune response had been viewed as comprising two different activities: a humoral and a cellular response. The humoral response is thought to consist primarily of the actions of soluble proteins, known as antibodies or immunoglobulins. The proteins have the capability of binding to, and assisting in the removal from body fluids of, matter perceived foreign (i.e., "non-self") through the recognition of antigenic sites on the foreign matter (known as an antigen). The cellular response is thought to consist of (as the name implies) cell mediated activities, for example macrophage phagocytosis and lymphocyte involvement in delayed-type hypersensitivity and allograft reactions. However, extensive research has proven that while humoral and cellular immunity individually may represent the final stages of an immune response, the entire response revolves around a series of very complex, network-like interactions of lymphocytes, macrophages and other cells acting in concert with each other and with immunoglobulins. Moreover, immunologists now hold the opinion that other soluble proteins (e.g., the so-called lymphokines produced by lymphocytes) play a critical role in controlling the sequence of events making up immunity.

Lymphokines apparently mediate cellular activities in a variety of ways. They have been shown to have the ability to support the proliferation and growth of various lymphocytes and, indeed, are thought to play a crucial role in the initial differention of pluripotential hematopoietic stem cells into the vast number of progenitors of the tremendously diverse immunologic cellular lineages. Cell lineages thought to be controlled in part lymphokines include two types of lymphocytes: B cells that can differentiate to produce and secrete the five major classes of immunoglobulins ($\alpha$, $\delta$, $\gamma$, $\epsilon$, and $\mu$; known as the IgA, IgD, IgG, IgE, and IgM isotypes, respectively), and T cells of various subsets that through various means induce or suppress B cells and some of the other cells (including other T cells) making up the the immune network.

Another important cell lineage whose growth seems to be under partial control of lymphokines is the mast cell—a granule-containing connective tissue cell located proximate to capillaries throughout the body, with especially high concentrations in the lungs, skin, gastrointestinal and genitourinary tracts. Mast cells play a central role in allergy-related disorders, particularly anaphylaxis. Briefly stated, once certain antigens cross-link IgE class immunoglobulins bound to receptors on the mast cell surface, the mast cell degranulates and releases mediators (e.g., histamine, serotonin, heparin, kinins, etc.) which can cause anaphylactic and some other allergic reactions.

The inhibition of mast cell degranulation by blocking IgE binding has been reported (U.S. Pat. No. 4,161,522), but attempts to duplicate the experiments have been unsuccessful (Bennich, H. et al. Int. Archs. Allergy Appl. Immun. 53: 459–468 [1977]), although experimentation continues. Recently, however, clinical research to better understand (and thus potentially treat therapeutically) allergies, anaphylaxis, and other IgE related immune disorders has focused more on the mechanisms of IgE formation.

Ontogenetic studies of lymphocytes have demonstrated the presence of B cells in fetal liver and spleen. In rodents, B cells initially exhibit surface IgM, but shortly after birth a portion bear surface IgE. The differentiation of fetal B cells to IgE bearing cells appears to be independent of any antigen or T cells. However, the subsequent differentiation of IgE bearing cells to IgE secreting cells seems dependent on exposure to the antigen against which the B cell can make specific antibodies and to which a set of T cells can also bind (see generally, Ishizaka, K., Annals of Allergy 48: 320–324 [1982]). (This process may occur for other isotypes as well.)

Therefore, with no practical, readily apparent method known for halting the post-natal development of IgE bearing B cells, physicians have attempted to regulate the 0 response by antigen-specific inactivation of IgE bearing B cells or the associated T cells. This has entailed injecting modified antigens into allergic patients, a procedure which in some cases risks anaphylactic shock or reduction of other needed immune response capability. Moreover, many people develop allergy to a variety of different antigens, which would require a multitude of modified antigen preparations and injections. For these and other reasons, antigen specific inactivation has been at best moderately successful, but research work is continuing.

Within the last few years, a few research groups have reported the existence of soluble, lymphocyte-secreted, regulatory factors that appear to act selectively on the IgE response, but which are not antigen-specific. These factors have been only partially characterized, with three research groups reporting molecular weights ranging from about 15,000 to 60,000 to 200,000 daltons. (See, Katz, D. Immunology 41: 1–24 [1980]). At present, the relationship (or lack thereof) among the factors is not known with certainty, although they appear to be antigen non-specific and either suppressive or enhancing with respect to the IgE response. Unfortunately, research to partly characterize these factors has been hampered by a lack of sufficient quantities of factor to conduct extnesive protein analysis, as well as by assay procedures that are difficult, thime consuming and, in some cases, potentially subjective.

In spite of these drawbacks, research has progressed, albeit more slowly than if the materials were available in bulk. The best characterized factors are the so-called IgE binding factors (IgE-BF), which—as their name implies—have affinity for IgE. They are postulated to function by first binding to IgE-bearing B cells via surface IgE, and then through a complex, poorly understood series of events, to affect the differentiation of the B cells to IgE secreting plasma cells. Apparently, as IgE-BF's do not bind to other immunoglobulin bearing B cells, the factors are isotype specific.

At least two measurably active types of IgE-BF have been defined. These two factors have very similar molecular weights (about 15,000 daltons) and similar affinity for IgE. They seem to differ primarily in their carbohydrate moieties, with one, IgE-potentiating factor, probably containing N-linked mannose-rich oligosaccharide and having terminal sialic acid; whereas the second, IgE-suppressor factor, is probably O-glycosydically linked and has a terminal galactose sugar. Interestingly, it seems that one T cell set has the capacity to form either factor, the particular factor produced (or perhaps another IgE-BF with no detectable IgE suppressor or potentiating activity) being dependent on the cell's environment. (See generally, Ishizaka, K., Lymphokines 8: 41–80 [1983].)

The research described immediately above has opened new and exciting vistas in the potential control of IgE levels. However, a full investigation of the proposed relationship between the two binding factors and their activities will probably necessitate ascertaining additional structural data, e.g., substantially complete sequence analysis of the molecules in question. Protein sequencing offers, of course, a possible means to solve the problem, but it is very difficult work experimentally, especially on small quantities of material, and to date has not proved useful. Having the capability of making bulk quantities of polypeptides exhibiting mammalian IgE-BF activity is probably essential to understand the factors' modes of action and may further serve to facilitate greatly the study of the biology of isotype regulation in general. Accurate and complete sequence data on a rodent IgE-BF will also aid in the search for human IgE-BF proteins, enhancing the likelihood of treatment for IgE mediated diseases. Finally, additional information on any lymphokine will assist in evaluating the roles of the various factors and cells of the immune network, providing insight into the entire immune system - with the concomitant therapeutic benefits.

Thus, there exists a significant need for extensive nucleotide sequence data on the DNAs coding for, and amino acid sequences of, proteins exhibiting IgE-BF activity, as well as a simple and economic method of making substantial quantities of such material. The present invention fulfills these needs.

SUMMARY OF THE INVENTION

The present invention provides cDNA clones coding for at least a major portion of polypeptides exhibiting mammalian immunoglobulin binding factor activity and, more specifically, IgE binding factor (IgE-BF) activity. A nucleotide sequence for one of the cDNAs and a putative amino acid sequence for the associated polypeptide are shown in FIG. 1. The cDNA sequences can be integrated into various vectors, which in turn can direct the synthesis of the corresponding polypeptides in a variety of hosts, including eukaryotic cells, such as mammalian cells culture.

More specifically, the invention provides a process for producing a polypeptide exhibiting rodent IgE-binding factor activity, the process comprising the steps of:
(a) providing a vector comprising a nucleotide sequence coding for said polypeptide, wherein the nucleotide sequence is capable of being expressed by a host containing the vector;
(b) incorporating the vector into the host; and
(c) maintaining the host containing the vector under conditions suitable for expression of the nucleotide sequence into the polypeptide.

Preferably, the cDNA sequences are derived from a cell (such as a T cell hybridoma) containing the mRNA sequences coding for the polypeptides, and the host is an organism, such as a eukaryotic cell transfected or transformed with the vector. Further, the vector also preferably comprises a second nucleotide sequence capable of controlling expression of the nucleotide sequence coding for the polypeptide. This second sequence can include a promoter sequence, one or more intron sequences and a polyadenylation sequence, to permit, respectively, transcription, splicing and polyadenylation of the nucleotide sequence coding for the polypeptide.

Particularly, when the host is a mammalian cell, such as a Cos7 monkey cell, the vector contains the promoter sequence of the simian virus 40 (SV40) early region promoter and the polyadenylation sequence of the SV40 late region polyadenylation sequence. This vector permits expression of IgE-BF activity in Cos7 cells after transient transfection of the appropriate cDNA clones.

Another aspect of the present invention are the cDNA's from, for example, a human cDNA or genomic library, and which code for other mammalian immunoglobulin binding factors. It is noted that a few of the described rodent cDNA sequences seem to encode activities that are not exhibited by the cell line that the cDNAs were derived from.

The polypeptide of FIG. 1 and other polypeptides encoded by some of the cDNAs of the present invention are capable of enhancing the differentiation of IgE bearing B cells into IgE secreting cells, particularly in vitro. Suitable pharaceutical compositions for this and other uses can be prepared by adding the polypeptides to therapeutically compatible carriers.

Additional features and advantages of the invention will become apparent from the following detailed description, which describes, by way of example, the present invention.

BRIEF DESCRIPTION OF THE FIGURES

FIG. 1 illustrates the nucleotide sequence and putative corresponding amino acid sequence of a cDNA clone exhibiting IgE binding factor activity.

DESCRIPTION OF THE SPECIFIC EMBODIMENTS

Figure 2:
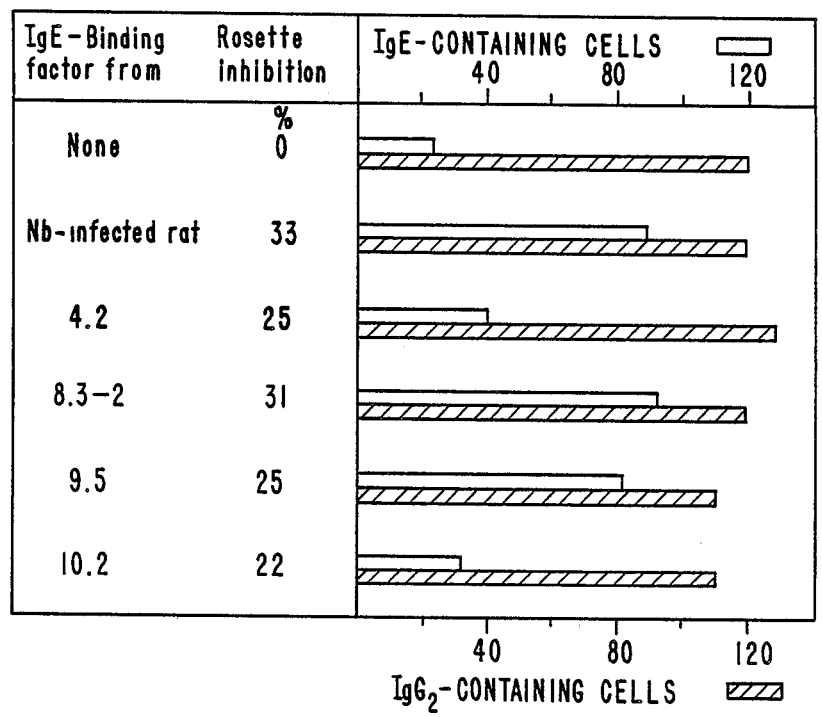
FIG. 2 depicts the amount of IgE potentiating activity in four of the cDNA clones of the present invention. (8.3-2 is an individual preparation of clone 23B6p8.3.) IgE- and IgG2-forming cells per $10^6$ total cells are indicated.

In accordance with the present invention, complementary DNA (cDNA) clones are provided for polypeptides exhibiting mammalian IgE binding factor (IgE-BF) activity. After the cDNA sequences have been incorporated in replicable expression vectors, and the vectors transfected into an appropriate host (e.g., a mammalian cell in culture), the expressed polypeptides have the ability selectively to bind IgE. Moreover, some of the expressed polypeptides can also enhance the differentiation of IgE bearing B cells into plasma cells secreting IgE. An exemplary, putative amino acid sequence based on the experimentally determined nucleotide sequence of one cDNA clone is shown in FIG. 1. The amino acid sequence commences with a hydrophobic leader region typical of secreted and membrane-bound proteins. Furthermore, there exist at least two potential sites for N-glycosylation (Asn-X-Thr; Neuberger et al., Glycoproteins 5, 450-490, Elsevier Publishing Co., U.S.A. [1972]), as well as possible sites for O-glycosylation.

A total of four cDNA clones which encode IgE-binding factor activity have been isolated from a rat-mouse T-hybridoma cell line. These cDNA clones were identified first by hybrid selection and translation of IgE-binding factor activity in *Xenopus laevis* oocytes, and then by direct expression in transfected Cos7 monkey cells.

The clones were isolated in the absence of amino acid sequence information on the IgE-BF's and without a suitable antiserum for assay purposes. Surprisingly, although the hybridoma serving as the mRNA source for the cDNA clones secreted only (under the conditions utilized) IgE-BF having IgE suppressive activity or IgE-BF with no detectable suppressive or potentiating activity, two of the isolated clones direct expression in Cos7 cells of IgE-BF having IgE potentiating factor activity. This finding lends considerable support to the likelihood that one criterion determining the biological activities of the IgE-BF's may be the extent and type of glycosylation.

A variety of methods may now be utilized to prepare the cDNAs of the present invention. By way of example, total mRNA is extracted (e.g., as reported by Chirgwin, J. et al, Biochemistry 18: 5294-5299 [1979]) from a cell line, which can be a hybrid cell line, producing polypeptides exhibiting mammalian IgE-BF activity. The double-stranded cDNAs from this total mRNA are constructed by using primer-initiated reverse transcription (Verma, I., Biocheim. Biophys. Acta, 473: 1-38 [1977]) first to make the complement of each mRNA sequence, and then priming for second strand synthesis (Land, H. et al., Nucleic Acids Res., 9: 2251-2266 [1981]). Subsequently, the cDNAs can be cloned by joining them to suitable plasmid or bacteriophage vectors (Rougeon, F. et al., Nucleic Acids Res., 2, 2365-2378 [1975] or Scherer, G. et al., Dev. Biol. 86, 438-447 [1981]) through complementary homopolymeric tails (Efstratiadis, A. et al., Cell, 10, 571-585 [1977]) or cohesive ends created with linker segments containing appropriate restriction sites (Seeburg, P. et al., Nature, 270, 486-494 [1977] or Shine, J. et al., Nature, 270, 494-499 [1977]), and then transforming a suitable host. (See generally, Efstratiadis, A., and Villa-Komoroff, L., "Cloning of Double Stranded cDNA", in Setlow, J. and Hollaender, A. [eds.] Genetic Engineering, Vol. 1, Plenum Publishing Corp., N.Y., U.S.A. [1982].)

A preferred method of obtaining the full-length cloned cDNAs of this invention is the procedure developed by Okayama, H. and Berg, P. (Mol. Cell. Biol., 2: 161-170 [1982]). This method has the advantage of placing the cDNA inserts in a bacterial cloning vector and in a position whereby the cDNA can also be directly translated and processed in mammalian cells. Briefly, the first cDNA strand is primed by polydeoxythymidylic acid covalently joined to one end of a linear plasmid vector DNA. The plasmid vector is later cyclized with a linker DNA segment that bridges one end of the plasmid to the 5' end of the cDNA coding sequence. By employing a DNA fragment containing the Simian Virus 40 (SV40) early region promoter and a modified SV40 late region intron, the cDNA can be expressed without further modification in vitro in Cos7 monkey kidney cells. (See generally, Okayama, H. and Berg, P., Mol. Cell. Biol., 3: 280-289 [1983] and Jolly, D. et al., Proc. Nat. Acad. Sci. U.S.A., 80: 477-481 [1983].)

The cDNA libraries can be screened by hybrid selection (Harpold, M. et al., Nucleic Acid Res., 5: 2039-2053 [1978] or Parnes, J. et al., Proc. Nat. Acad. Sci. U.S.A., 78: 2253-2257 [1981] and translation in Xenopus oocytes (Aurdon, J., Nature, 233: 177-182 [1971]). (See generally, Villa-Komaroff, L. et al., Proc. Nat. Acad. Sci. U.S.A., 75: 3727-3731 [1978].)

Once the cDNA library in the Okayama/Berg plasmid vector has been completed, the cDNA clones are collected and random pools checked for the presence of the desired cDNAs by hybrid selection, translation, and assay (e.g., by measuring mast cell growth factor activity, the existence of antigenic determinants, or other biological activities). Pools positive by these criteria can then be probed with an appropriate subtracted probe, e.g., cDNA from an induced T cell line. Thereafter, the positive, probed pools are divided into individual clones which are tested by transfection into a suitable host (such as a mammalian cell culture), and the host supernatant assayed for IgE-BF activity. Positive clones are then sequenced.

In further describing the procedures relating to preparing cDNA clones of the invention, the mRNA source cells will be considered first, followed by general descriptions of the procedures of the in vitro translation of mRNA coding for a protein exhibiting IgE-BF activity; the construction of a cDNA library containing the cDNA sequences; hybrid selection of the library; isolation of full-length cDNA clones in a plasmid vector and subsequent expression in mammalian cells; human IgE-BF isolation expression in bacteria and yeast; and purification and cell culture and formulation. A more detailed description of the entire experimental process will follow thereafter.

Cell Lines

Suitable cells for use in connection with isolating the cDNA clones of the present invention are those that can be shown to make mRNA encoding IgE-BF's. A prepared cell source is the 23B6 cloned line (Huff et al. J. Immunol. 129: 509–514 [1982]) deposited at the American Type Culture Collection (ATCC accession number HB8521) but neither hybridomas nor cell cultures are mandatory. Other sources of immunoglobulin binding factors include the human B lymphocytoma RPMI 8866 (Chen, P. et al., J. Immunol. Meth. 58: 59–71 [1983]), human peripheral blood lymphocytes (Lethibichthuy et al., Eur. J. Immunol. 10: 894–898 [1980]), and a mouse hybridoma line (Lowy, I. et al., P.N.A.S. USA 80: 2323–2327 [1983]).

Isolation and Size Fractionation of mRNA

Total cellular mRNA can be isolated by a variety of methods, e.g., by using the guanidinium-thiocyanate extraction procedure of Chirgwin et al. (Biochemistry, 18: 5294–5299 [1979]). If this method is utilized, approximately 100 µg of polyA+mRNA, selected on columns of oligo (dT) cellulose, is obtained from $1-2 \times 10^9$ cells, such as the 23B6 hybridoma.

Hybrid Selection and Microinjection of Xenopus laevis Oocytes

Filter hybridizations are preferably performed essentially as described by Parnes et al. (Proc. Natl. Acad. Sci. U.S.A., 78: 2253–2257 [1981]). Aliquots of eluted mRNA are injected into individual Xenopus laevis oocytes by methods well known in the art. Supernatants from viable oocytes are collected after 48 hr, pooled and assayed for IgE-BF activity.

Construction of cDNA Library

The cDNA library can best be constructed using the pcDV1 vector-primer and the pL1 linker fragment (available from P-L Biochemicals Inc., Milwaukee, Wis.) according to procedures which result in greatly enriched full-length copies of mRNA transcripts, e.g., Okayama, H., and Berg, P. (Mol. Cell. Biol., 2: 161–170 [1982] and Mol. Cell. Biol., 3: 280–289 [1983]). The plasmid vector, which contains SV40 early promoter and SV40 RNA processing signals, is designed to promote expression of the cloned cDNA segment in mammalian cells.

Using the Okayama and Berg procedure, the cyclized vector-cDNA preparation is transformed into a competent bacterial cell, such as E. coli MC1061 cells (Casadaban, M. and Cohen, S., J. Mol. Biol., 138: 179–207 [1980] using calcium chloride (Cohen, S. et al., Proc. Nat. Acad. Sci. U.S.A., 69: 2110–2114 [1972]). Starting with 5 µg of polyA+ RNA from 23B6 cells, about $1 \times 10^5$ independent transformants are obtained. If desired, sublibraries based on the size of cDNA insert may be prepared from total cDNA library as described in Okayama, H. and Berg, P. (Mol. Cell Biol., 3, 280–289 [1983]). All nucleotide sequencing can be performed according to the procedures of Maxam, A. and Gilbert, W. (Methods Enzymol., 65: 499–560 [1980]) and Sanger et al. (J. Mol. Biol. 143, 161–164 [1980]).

Preparation of Subtracted cDNA Probe

A $^{32}$P-cDNA probe is enriched for hybridoma-specific sequences by one cycle of cDNA adsorption (Davis, M. et al., "Isolation of B and T-Cell Specific Genes", Vitteta, E. and Fox, C. (eds.), UCLA Symp., pg. 48 [1982]). A radioactively labeled first strand cDNA is prepared by reverse transcription of about 5 µg poly(A)+RNA from 23B6 cells cultured with IgE. This cDNA is allowed to hybridize to about 50 µg of poly(A)+RNA from an appropriate screening line to cot > 1500, and then fractionated on a hydroxylapatite column. The unabsorbed fraction, which can include both nonhybridizable material and single-stranded cDNA, can comprise 10–12% of the total cDNA mass. This material may then be concentrated ten-fold by repeated extraction with n-butanol and stored at 4° C. prior to use as a plaque hybridization probe (Maniatis, T. et al., "Molecular Cloning, A Laboratory Manual", Cold Spring Harbor Laboratory, U.S.A. [1982]).

DNA Transfections into Monkey Cells

Approximately $1 \times 10^6$ Cos7 monkey fibroblast cells are seeded onto 100 mm plates the day prior to transfection. Transfections are best performed with 50 µg of plasmid DNA in 4.0 ml of DME containing 50 mM Tris.HCl, pH 7.4, and 400 µg/ml DEAE-Dextran (Pharmacia Fine Chemicals, Uppsala, Sweden). This solution is then removed after 4 hr and relaced with 7.0 ml DME+4% fetal calf serum. The medium is collected after 72 hr and assayed for IgE-BF activity as described above.

Assay of IgE-Binding Factor Activities.

(i) IgE binding factors may be assayed initially by their ability to inhibit formation of IgE-specific rosettes by lumphocytes and fixed ox red blood cells which had been sensitized with IgE (Yodoi, J. and Ishizaka, K. J. Immunol. 122: 2577 [1979]; 124: 1322 [1980]). The variation between replicate assays of a given sample should be less than ±10% of the average values of these experiments. Supernatants from uninjected oocytes or mock-transfected Cos7 cells can serve as negative controls. (ii) IgE-binding factors in the supernatants of injected oocytes and transfected Cos7 cells can be purified by affinity chromotography on IgE-coupled Sepharose (Yodoi, J. et al, J. Immunol. 125: 1436–1441 [1980]). The specificity of these binding factors for IgE is established by demonstrating their inability to bind to IgG-coupled Sepharose or BSA-coupled Sepharose. (iii) IgE-BF can be tested for isotype-specific suppression and potentiation in in vitro cultures of antigen-primed lymph node cells. The suppressive and potentiating activities of IgE-BF were originally defined by their effect on the number of IgE-producing cells in an in vitro culture of antigen-primed rat mesenteric lymph node cells (Suemura et al., J. Immunol. 125: 148–154 [1980]; Hirashima et al., J. Immunol. 125: 1442–1448 [1980]; Yodoi et al., J. Immunol. 128: 289–295 [1982]).

While most of the assays have been described in terms of measuring rodent IgE-BF, human IgE-BF assays are available (Ishizaka, K. and Sandberg, K., J. Immunol. 126: 1692–1696 [1981]). Indeed, rapid screening assays for human IgE-BF are available (Chen, P. et al., J. Imm. Meths. 58: 59–71 [1983]).

Human IgE-BF cDNA Isolation

DNA clones of rodent genes have been used to identify and isolate DNA encoding the homologous human genes. Because of the relatively low degree of homology between human and rodent genes, the stringency of hybridization conditions must be adjusted to allow for cross-hybridization between sequences which are only 75-80% homologous. Several different experimental protocols have been used to achieve this purpose. For example, the human Cκ immunoglobulin light chain gene has been isolated using the corresponding mouse Cκ gene as a probe (Hieter, P. et al., Cell 22: 197-207 [1981]) and mouse transplantation antigen genes have been isolated by hybridization to DNA clones encoding their human counterparts (Steinmetz, M. et al., Cell 24: 125-134 [1981]).

A preferred method entails plating λ phage clones from a library of human geomic DNA (Maniatis, T., et al., "Molecular Cloning, A Laboratory Manual", Cold Spring Harbor Laboratory, U.S.A. [1982]) at a density of $2 \times 10^4$ to $5 \times 10^4$ plaques per 150 mm plate on an appropriate host strain, such as *E. coli* LE392. Ten to twenty plates are generally sufficient.

After 10-12 hours incubation at 37° C., the plates are refrigerated for two hours, then a 132 mm nitrocellulose filter is applied to the agar surface of each plate. The filter is allowed to remain in contact with the plate for at least five minutes, during which time the filters are keyed to the plates by puncturing with an ink-filled 22-gauge needle. The filters are then peeled from the plates and incubated successively for at least two minutes in first 250 ml of 0.1 N NaOH, 0.5M NaCl; then in 250 ml of 0.5M Tris.HCl pH 7.5, 1.5M NaCl. The filters are dried on paper towels and then baked at 80° C. for 4-8 hours.

For hybridization, the filters are wetted in 1x SET (0.15M NaCl, 30 mM Tris.HCl pH 8.0, 1 mM Na2 EDTA), then incubated in a solution of 3x SET, 5x Denhardt's (Denhardt, D.T., B.B.R.C. 23: 641-646 [1966]), 10% dextran sulfate, 0.1% SDS, and 50 μg/ml each poly (rA), poly (rC), and poly (rG), at 65° C. for 2 hours (1.5-2 ml/filter) with constant agitation. This solution is then discarded, and the filters are hybridized with 0.5 μg ($\cong 10^8$ cpm) of a nick-translated mouse DNA probe in the same solution (fresh), 1.5-2 ml/filter at 65° C. for 1 hour, then at 55° C. for 12-20 hours. The filters are then washed successively in 3x SET, 1x Denhardt's, 0.1% SDS; and 1x SET, 0.1% SDS (10-15 ml/filter) at 55° C., each for one hour with gentle agitation. The filters are dried on paper towels, then autoradiographed for 12-24 hours with appropriate film and an intensifying screen. Hybridizing plaques are picked from the agar plates with sterile pasteur pipets, and each is expelled into 1 ml of 0.1M NaCl, 0.01M Tris.HCl pH 7.5, 10 mM MgCl2, 100 μg/ml gelatin, with 50 μl of CHCl3 added. After at least 4-8 hours in the cold, the phage from each plaque are rescreened at low density (2000-4000 plaques/ 150 mm plate) by a procedure identical to that described above.

Expression in *E. coli*, Yeast, and Cell Culture

Prokaryotes are very suitable for expression of IgE-BF polypeptides, assuming glycosylation is not desired. *E. coli* W3110 (F−, λ−, prototropic, ATTC No. 27325), *E. coli* K12 strain 294 (ATCC No. 31446), *E. coli* χ1776 (ATCC No. 31537), bacilli such as *Bacillus subtilus*, and other enterobacteriaceae such as *Salmonella typhimurium* or *Serratia marcescens*, and various Pseudomonas species may be used as hosts.

To obtain high expression levels, promoters should be utilized, such as the β-lactamase (penicillinase) and lactose promoter systems (Chang et al., *Nature*, 275: 615 [1978]; Itakura et al., *Science*, 198: 1056 [1977]; Goeddel et al., *Nature* 281: 544 [1979]) or a tryptophan (trp) promoter system (Goeddel et al., *Nucleic Acids Res.*, 8: 4057 [1980]). While these are the most commonly used, other microbial promoters are available.

In addition to prokaryotes, those skilled in the art will realize that eukaryotic microbes, such as yeast, may also be used in IgE-BF production. *Saccharomyces cerevisiae* is the preferred eukaryotic microorganism. For expression in Saccharomyces, the plasmid YRp7, for example (Stinchcomb, et al, *Nature*, 282: 39 [1979]; Kingsman et al, *Gene*, 7: 141 [1979]; Tschemper et al., *Gene*, 10: 157 [1980]), is commonly used. Suitable promoting sequences in yeast vectors include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; Holland et al., *Biochemistry*, 17: 4900 [1978], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization. Any plasmid vector containing a yeast-compatible promoter, an origin of replication and termination sequences is suitable.

In addition to microorganisms, cell cultures derived from multicellular organisms (especially mammalian cells) may also be used as hosts. Examples of such useful host cell lines are HeLa cells, Chinese hamster ovary cell lines, and baby hamster kidney cell lines. Expression vectors for such cells ordinarily include, as necessary, an origin of replication, a promoter located in front of the gene to be expressed, along with any required ribosome binding sites, RNA splice sites, polyadenylation sites, and transcriptional terminator sequences. When used in mammalian cells, the expression vector's control functions are often provided by viral material. For example, commonly used promoters are derived from polyoma, Adenovirus 2, and most frequently Simian Virus 40.

When utilizing eukaryotic systems for IgE-BF production, the host's glycosylation capability should be considered, given the apparent importance of glycosylation to the function of IgE-BF's.

Purification and Formulations

The IgE-BF polypeptides expressed in *E. coli*, yeast or otherwise can be purified according to standard procedures of the art, including ammonium sulfate precipitation, fractionation column chromatography (e.g., ion exhange, gel filtration, electrophoresis, affinity chromatography, etc.) and ultimately, crystallization (see generally, "Enzyme Purification and Related Techniques", Methods in Enzymology, 22: 233-577 [1971]). Once purified, partially or to homogeneity, the IgE potentiating factor polypeptides of the invention may be utilized in pharmaceutical compositions (see below), e.g., for treating parasitic infections. Generally, IgE-BF's may be used for research purposes, e.g., as a reagent specific for IgE B cell differentiation or as a replacement for anti-IgE antibodies in assay systems, or as an antigenic substance for eliciting specific immunoglobulins useful in immunoassays, immunofluorescent stainings, etc., for IgE related studies. (See generally, "Immunological Methods", Vols. I & II, Eds. Lefkovits, I. and Pernis, B., Academic Press, New York, N.Y. [1979 & 1981]; and "Handbook of Experimental Immunology", Ed. Weir, D., Blackwell Scientific Publications, St. Louis, Mo. [1978]).

For preparing pharmaceutical compositions containing the polypeptides described by this invention, such polypeptides are combined in a mixture with preferably inert, pharmaceutically acceptable carriers. Suitable carriers and processes for their preparation are well known in the art (see, e.g., Remington's Pharmaceutical Sciences and U.S. Pharmacopeia: National Formulary, Mack Publishing Company, Easton, Pa. [1980]). The preferred course of administration is parenteral and can include mechanical delivery systems.

Preferably, the pharmaceutical composition is in unit dosage form. In such form, the preparation is subdivided into unit doses containing appropriate quantities of the active component. The quantity of active compound in a unit dose of preparation may be varied or adjusted from 1 μg to 100 mg, according to the particular application and the potency of the active incredient. The composition can, if desired, also contain other therapeutic agents. The dosages may be varied depending upon the requirement of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

Isolation of Homologous Genes Encoding Other Immunoglobulin Binding Factors

Isolation of homologous genes can be accomplished by the following procedure. A library of rat genomic DNA in a λ phage (Maniatis, T. op. cit. [1982]) or cosmid (Steinmetz et al., Cell 28: 489–498 [1982]) vector is screened with a nick-translated $^{32}$P-labelled restriction fragment of clone 23B6p8.3 (FIGS. 1 and 2). Hybridizing clones are picked and purified, DNA is prepared, and restriction endonuclease mapping performed. Alternatively, a pCD cDNA library could be constructed from a cell line expressing other isotype-regulatory factors, such as the $T_2D_4$ mouse hybridoma (Lowy, I. et al., Proc. Nat. Acad. Sci. U.S.A. 80: 2323–2327 [1983]; Yodoi, J. et al., J. Immunol. 131: 303–310 [1983]), and screened as described above for isolation of individual cDNA clones.

DNA clones encoding other immunoglobulin binding factors must generally be identified by the activity of the protein which they encode. pCD cDNA clones from a cell line such as $T_2D_4$ would be introduced into Cos7 monkey cells and cell supernatants assayed as described in the above references. Genomic DNA clones in either λ phage or cosmid vectors could be used in cotransfection experiments with a separate piece of DNA encoding a selectable marker. For example, Goodenough, R.S. et al. (Science 215: 677 [1982]) identified the mouse $L^d$ transplantation antigen gene by such DNA-mediated gene transfer into a mouse Ltk− fibroblast cell line. The stably transformed cell lines thus generated are then screened for immunoglobulin binding factor production by the assays described in the above references for the $T_2D_4$ cell line.

The following experimental information and data are offered by way of example and not by way of limitation.

EXPERIMENTAL

A. Cloned Rat-Mouse T-Hybridoma Cells (1) Formation of rat-mouse T cell hybridomas.

Rat MLN cells were fused with HPRT-deficient AKR thymoma cells, BW5147, by the method of Kohler and Milstein (Kohler, G. and Milstein C. Eur. J. Immunol. 6: 511 [1976]). Briefly, $7.5 \times 10^7$ MLN cells were pelleted together with $2.5 \times 10^7$ BW5147 (ATCC accession #T1B48) cells. The pellet was gently dispersed, and 1 ml of a solution containing 50% polyethylene glycol 4000 (Sigma Chemical Co., St. Louis, Mo.) and 5% dimethyl sulfoxide was added during a period of 1 min with constant swirling. The cell suspension was swirled gently for 90 sec at 37° C. followed by the gradual addition of Hanks' balanced salt solution (BSS). After fusion, cells containing $2 \times 10^5$ MLN cells were resuspended in HAT-containing culture medium and were seeded in each well of 96-well plates. Culture medium was complete Dulbecco's modified eagle's medium (DME) that consisted of high glucose DME supplemented with antibiotics, 10% fetal calf serum (FCS, Flow Laboratories, McLean, Va.), 10% NCTC 135 medium (GIBCO, Grand Island, N.Y.), 10 mM HEPES buffer, 0.2 U/ml bovine insulin (Sigma), 50 μg/ml pyruvic acid, and 150 μg/ml oxaloacetic acid. Cells were kept in HAT-DME for 2 to 3 weeks until clones appeared, and hybrid cells were later maintained in complete DME with biweekly subculture. Aliquots of cells were frozen and stored in liquid nitrogen.

(2) Formation of IgE-binding factors.

Hybridoma cells were suspended at a concentration of $1 \times 10^6$ cells/ml in RPMI 1640 medium supplemented with 5% FCS, 3 mM L-glutamine, $5 \times 10^{-5}$ M 2-mercaptoethanol, and antibiotics, and were cultured for 24 hr in the presence or absence of 10 μg/ml of rat IgE. Cellfree supernatants were filtered through Diaflo CF 50A membranes or XM 50 membranes (cut-off point 50,000 m.w.; Amicon Corp., Lexington, Mass.). When necessary, the culture filtrates (CF) were concentrated by ultrafiltration with the use of YM-5 membranes.

B. Assays for IgE-Binding Factors (1) Inhibition of IgE-specific Rosette Formation (a) Fixed ox erythrocytes: A 10% suspension (1 ml) of ox erythrocytes (Colorado Serum Co., Denver, Colo.) in phosphate-buffered saline (PBS) was mixed with an equal volume of 0.2 mg/ml trypsin (Worthington Biochemical Co.) in PBS and incubated for 1 hour at 37° with occasioal mixing. A 2 ml aliquot of 0.2 mg/ml soybeam trypsin inhibitor (Worthington Biochemical Co.) in PBS was added. The cells were washed five times, each time with 1 ml PBS, then resuspended to 10% in 1 ml PBS. A 1 ml aliquot of 3% pyruvic aldehyde (ICN Pharmaceuticals) in PBS, pH 7.2 was added and the cells were incubated 20 hr at room temperature with continuous mixing on a rotator at 30 rpm. The cells were washed five times in PBS as above, and then incubated with 2 ml 3% formaldehyde (Fisher Scientific Co.) in PBS for 20 hr at room temperature. The fixed erythrocytes were washed five times with PBS as above, and stored at 4° C. as a 10% suspension in PBS.

(b) Fixed erythrocytes sensitized with IgE (IgE-RBC) or human serum albumin (HSA) (HSA-RBC): IgE was prepared from ascites fluids of rats or mice bearing rat IgE myeloma (IR183 or IR162; Baxin, H., et al., Immunology 26: 713 [1974] or mouse IgE hybridoma (ATCC Accession Nos. TIB141 and TIB142) tumors, respectively. The techniques of ammonium sulfate precipitation, DEAE-cellulose chromatography, and gel filtration are standard in the field (Mishell, B. and Shiigi, S. [eds.] "Selected Methods in Cellular Immunology", W. H. Freeman and Co. San Francisco Calif. [1980], pp. 278–280; Vander-Mallie et al. J. Immunol. 128: 2306–2312 [1982]). Since rodent IgE is acid-labile, care was taken to maintain pH>7.0 during these procedures. Fixed ox erythrocytes were washed once in 0.1M Na acetate, pH 5.0, and resuspended to 4% in this buffer. To 0.25 ml of 1 mg/ml rat or mouse IgE or HSA (2X crystallized, Nutritional Biochemicals) in borate buffered saline, pH 8.0 (PBS), was added 0.25 ml 0.1M Na acetate, pH 5.0, followed by 0.5 ml of the fixed erythrocyte suspension. This mixture was incubated 2 hr at room temperature on a rotator as described above. The sensitized cells were washed three times with 1 ml PBS and resuspended in 1 ml PBS (2%). This suspension could be stored on week at 4° C.

(c) $Fc_\epsilon R+$ lymphocytes: Lewis strain rats (Microbiological Associates) were infected with 2800–3000 *Nippostrongylus brasiliensis* larvae via a subcutaneous route as described by Ogilvie, G. (Nature 204: 91 [1964]). Mesenteric lymph node cells were obtained two weeks after infection, suspended in RPMI 1640+5% fetal calf serum (FCS), and passed through a glass wool column to remove dead cells and cell debris as described by Ishizaka, T. et al. (Cell. Immunol. 22: 248 [1976]). Alternatively, normal mouse spleen cells were teased into single-cell suspensions in RPMI 1640+5% FCS and passed over Sephadex G-10 to deplete adherent cells as described by Ly and Mishell (J. Immunol. Methods 5: 239 [1974]; and in Mishell and Shiigi, pp. 175–179). These preparations containing about 30% $Fc_\epsilon R+$ lymphocytes were adjusted to $1 \times 10^7$/ml before use in the assay.

(d) Inhibition test: HSA-RBC were used as a negative control for background in every case. PBS was used as a negative control in place of samples containing inhibitors of IgE-specific rosette formation. To a 5 ml polypropylene tube was added, in this order: 6 μl FCS, 15 μl of a 1% suspension of IgE-RGC, and 30 μl of the sample to be tested (usually culture medium or oocyte supernatant). The tube was gently vortexed to coat the bottom of the tube with the added materials, then placed on ice for 2 hr. A 15 μl aliquot of $Fc_\epsilon R+$ lymphocytes ($1 \times 10^7$ cells/ml, above), was added. The tube was gently vortexed, incubated 10 min, 37°, then gently vortexed again. The cells were pelleted by centrifugation at 100×g, 4° C., for 7 min, and the sample was incubated at 0° C. 8–10 hr. The sample was removed from 0° and gently mixed manually to disperse the cell pellet. A 9.2 μl aliquot of 0.13% toluidine blue in PBS +13% FCS was placed in a second polypropylene tube, and then 20 μl of the dispersed pellet added. This sample was mixed by stirring three times with the pipet tip. The stained cell suspension was transferred to a Fuchs-Rosenthal hemocytometer, and allowed to stand 2–3 min. Rosettes were scored as single lymphocytes bound to at least 3–4 IgE-RBC. Typically, a positive control (no inhibitor) gives 30–35% rosette-forming cells (RFC), while a negative, background control (HSA-RBC) gives 5–10% RFC. At least 300 lymphocytes from each of two replicates of each sample were counted. Inhibition of IgE-specific rosette formation was determined by $$\left(1 - \frac{RFC \text{ (inhibitor)} - \text{background}}{RFC \text{ (control)} - \text{background}}\right) \times 100\%.$$

The variation between replicate assays of a particular sample was less than 10% of the average value.

(2) Affinity chromatography on IgE-coupled Sepharose.

IgE-coupled Sepharose 4B was prepared by incubating 5 ml of cyanogen-bromide activiated Sepharose (Pharmacia) with 50 mg rat or mouse IgE overnight at 4° C. The reaction was quenched by addition of four volumes of 0.5M ethanolamine.HCl, pH 8.0. The Sepharose was washed with 3–4 volumes of PBS. Cos7 cell supernatants were concentrated 4–10 fold by ultrafiltration with a Diaflo UM2 membrane. A 1 ml aliquot of concentrated Cos7 supernatant or of Xenopus occyte supernatant was mixed wih 0.5 ml IgE-coupled Sepharose. The mixtures were rotated at room temperature for 90 minutes, then packed into an 0.7×4 cm column (Bio-Rad). The effluent was recovered for testing by the rosette-inhibition assay, and the column was washed with 4×1 ml aliquots of PBS. IgE-binding factors bound to the column were eluted with 4×1 ml of 0.1M Na acetate buffer, pH 4.0, at 4° C. The eluate was collected into 0.4 ml of 1M Tris.HCl, pH 8.4–8.6, so that the final pH of the eluate was between 7.0 and 8.0. This neutralized eluate was dialyzed against Click's medium in a 3000-mol. wt. cutoff membrane (Spectrum Medical Industries) at 4° C., and concentrated to 1 ml by ultrafiltration with a Diaflo UM-2 membrane.

(3) Assays for IgE-Specific Suppressive and Potentiating activites in vitro.

(a) Antigen-primed rat mesenteric lymph node cells: Crystalline ovalbumin (Nutritional Biochemical) and 2,4-dinitrobenzene sulfonic acid (Eastman Organic Chemical Corp.) were coupled by the method of Eisen (Meth. Med. Res. 10: 94 [1964]), to generate DNP-ovalbumin (DNP-OA) with an average of 6.2 DNP groups per ovalbumin molecule. Lewis strain rats (Microbiological Associates) were immunized twice with 5 μg DNP-OA in complete Freund's adjuvant (Suemura and Ishizaka, J. Immunol. 123: 918–924 [1978]at a four-week interval. Mesenteric lymph node (MLN) cells were obtained 2–3 weeks after the second immunization, by standard techniques (Mishell and Shiigi, pp. 12–14).

(b) In vitro cultures: MLN cells from DNP-OA primed rats were cultured in Click's medium (Click, R., et al., Cell. Immunol. 3: 264 [1972]) supplemented with 10% normal rat serum, 50 μM β-mercaptoethanol, 100 unit/ml penicillin, and 100 μg/ml streptomycin. Cultures were set up in flat-bottomed Micro-Test II culture plates (Falcon Plastics, Oxnard, Calif.). Each culture well contained $2 \times 10^5$ viable nucleated cells, 1 μg/ml DNP-OA and 0.1 ml of dialyzed, concentrated IgE-Sepharose eluate (previous section) in a total volume of 0.2 ml. These cultures were incubated 5 days at 37° C., in a humidified atmosphere of 5% $CO_2$ and 95% air.

IgE-Suppressive factor activity was assessed in a culture which also contained IgE-potentiating factor (Hirashima et al., J. Immunol. 125: 1442–1448 [1980]). In this case, each culture well contained, instead of 0.1 ml of the dialyzed, concentrated IgE-Sepharose eluate, 0.05 ml of this eluate and 0.05 ml of an IgE-potentiating factor preparation. This preparation was obtained as a dialyzed supernatant from a culture of MLN cells isolated from a Nippostrongylus infected rat on the fourteenth day of infection (Suemura and Ishizaka, op. cit. [1978]).

(c) Detection of immunoglobulin-containing cells:
Rabbit antisera against rat IgE (IR162; IR183) were obtained by standard techniques (Mishell and Shiigi, pp. 261–268). A rabbit antiserum specific for rat $IgG_2$ was prepared by the standard technique described by Suemura, M. and Ishizaka, K. (op. cit. [1979]). A fluorescinated IgG fraction of goat anti-rabbit IgG serum was purchased from Meloy Laboratories Inc., Springfield, Va.

Immunoglobulin-containing cells were enumerated by immunofluorescence by standard techniques (Ishizaka, K., et al., Cell. Immunol. 22: 248–261 [1976]; Mishell and Shiigi, pp. 297–303). Briefly, $1-3\times10^5$ cultured cells were layered on a glass slide by using a Shandon cytocentrifuge. Slides were fixed with acetone and hydrated in PBS. The smears were treated with anti-IgE or anti-$IgG_2$, followed by fluorescinated anti-rat IgG. Only intensely stained plasma cells and blast cells were enumerated. The experimental error for determination of the stained cells was ±15%.

C. Isolation of mRNA from 23B6 Hybridoma Cells (1) Total Cellular m RNA

Cells from uninduced or IgE-induced 23B6 cultures ($1.5\times10^9$ cells; 1 liter culture) were washed in 100 ml cold PBS, and suspended in 5 ml cold PBS. The suspension was lysed in 80 ml guanidinium thiocyanate lysis solution (Chirgwin, J. M., et al, Biochemistry 18: 5294–5299 [1979]). The DNA was sheared by 4 passes through an 18-gauge needle. Lysate was layered on top of 14 ml 5.7M CsCl, 10 mM EDTA, pH 7 in 40 ml polyallomer centrifuge tubes and centrifuged in a Beckman SW28 rotor (Beckman Instruments, Inc., Palo Alto, Calif.) for 40 hr at 15° C., 25,000 rpm. The guanidinium thiocyanate phase containing DNA was pipetted off from the top, down to the interface. The walls of the tube and interface were washed with 2–3 ml of lysis solution. The tube was cut below the interface with a razor blade, and the CsCl solution decanted. RNA pellets were washed once with 1.5 ml cold 75% ethanol. Pellets were resuspended in 400 µl 10 mM Tris pH 7.5, 1 mM EDTA, 0.1% SDS. The solution was extracted once with 1:1 phenol:chloroform and 40 µl of 2M potassium acetate pH 5.0 added. RNA was precipitated with 1 ml of ethanol. RNA was collected by centrifuging and the pellets were washed once with cold 75% ethanol.

(2) Cytoplasmic mRNA.

$1.5\times10^9$ cells (one liter culture) were pelleted and washed in 100 ml of cold PBS. The cells were then suspended in 10 ml cold 0.1M Tris.Cl, pH 7.6, 0.15M NaCl, 1.5 mM $MgCl_2$. A 1.8 ml aliquot of 10% NP40 was added and the suspension was mixed gently. The cell lysate was underlaid with 5 ml of 15% sucrose, 1% NP40 in the above buffer. Nuclei were pelleted for ten minutes at 4° C. The supernatant was removed into an equal volume of 7M urea, 10 mM Tris.Cl, pH 7.6, 0.35M NaCl, 1% SDS and mixed by inversion. This lysate was extracted twice with phenol:chloroform (1:1) and RNA was precipitated by addition of 2.5 volumes of ethanol.

(3) Poly A+ mRNA isolation.

Washed and dried total RNA pellet was resuspended in 900 µl of oligo(dT) elution buffer (10 mM Tris-Cl, pH 7.4, 1 mM EDTA, 0.5% SDS). RNA was heated for 3 min. at 68° C., then chilled on ice. 100 µl of 5M NaCl was added. The RNA sample was loaded on a 1.0 ml oligo(dT) cellulose column (Type 3, Collaborative Research, Waltham, Mass.) equilibrated with binding buffer (10 mM Tris-Cl, pH 7.4, 1 mM EDTA, 0.5M NaCl, 0.5% SDS). Flow-through from the column was passed over the column twice more. The column was then washed with 20 ml binding buffer. Poly A+ mRNA was collected by washing with elution buffer. RNA usually eluted in the first 2 ml of elution buffer. RNA was precipitated with 1/10 volume 2M potassium acetate, pH 5, and 2.5 volumes of ethanol. The RNA pellet was collected by centrifugation, washed twice with cold ethanol, and dried. The pellet was then resuspended in water. Aliquots were diluted, and absorbance at 260 nm was determined.

D. Oocyte Injection

Oocytes were removed from female *Xenopus laevis* and incubated in Barth's solution (88 mM NaCl, 1 mM KCl, 0.33 mM $Ca(NO_3)_2$, 0.41 mM $CaCl_2$, 0.82 mM $MgSO_4$, 2.4 mM $NaHCO_3$, 10 mM HEPES (pH 7.9)). Injection clusters of 2-3 oocytes were prepared. RNA samples to be injected were dissolved in injection buffer (40 mM Tris-Cl pH 7.4, 0.35M NaCl). Total poly A+ mRNA was resuspended at a concentration of 500 µg/ml in injection buffer, while RNA samples eluted from DNA filters from hybrid selections (see below) always contained 5 µg of calf liver tRNA as carrier and were resuspended in 2 µl of injection buffer. 40 nl aliquots were injected into each oocyte using micropipets pulled by hand with tips forged using a microforge. The pipets were calibrated with known volumes of sterile $H_2O$. Approximately 30–40 oocytes were injected for each mRNA sample. The injected oocytes were incubated in groups of two or three in individual wells of 96-well microtiter dishes containing 10 µl of Barth's solution+1% bovine serum albumin per oocyte. The oocytes were kept at 19° C. for 48 hours, then the supernatants from wells containing viable oocytes were collected and pooled. These supernatants were sterilized by centrifuging for 10 minutes in a microcentrifuge, then assayed for IgE binding factor activity as described above. Supernatants from uninjected oocytes were always collected as a control.

As shown in Table I, injection of RNA from IgE-treated ("induced") 23B6 cells resulted in appearance in the supernatant of material which inhibited 40–60% of IgE-specific rosettes. All of this rosette-inhibiting activity was absorbed by IgE-coupled Sepharose, and the absorbed activity could be recovered by elution at pH 4.0 (as described above). The activity did not absorb to IgG- or BSA-coupled Sepharose. In contrast, supernatants from oocytes injected with RNA from 23B6 cells cultured without IgE ("uninduced") and from BW5147 cells contained no detectable IgE-binding factor activity, and inhibited only 5–7% of IgE-specific rosettes.

TABLE I
In Vitro Translation of IgE-Binding Factor Activity in Xenopus Oocytes

| RNA | IgE-specific rosette inhibition, % | IgE-Sepharose effluent | IgE-Sepharose eluate |
|---|---|---|---|
| 23B6 (induced) | 40-46% | 3 | 25 |
| 1:3 dilution[a] | 29% | — | — |
| 1:10 dilution[a] | 7% | — | — |
| 23B6 (uninduced) | 5-7% | — | — |
| BW5147 | 5-6% | — | — |
| Water | 3-4% | — | — |

[a]Dilutions of oocyte supernatants were also tested in the rosette-inhibition assay.

E. Construction of cDNA Libraries (1) A cDNA library of 23B6 induced RNA was constructed in the lambda phage vector λgt10. poly(A)+-RNA in water (5 μg, 10 μl) was heated to 65° C. for three minutes, then placed at room temperature. The following reagents were added in the indicated order: 4 μl 200 μg/ml oligo(dT)$_{12-18}$; 2 μl 25 mM dNTPs; 13 μCi α-$^{32}$P-dCTP (800 Ci/mmol); 2 μl of 10X reverse transcription buffer (Okayama, H. and Berg, P. Mol. Cell. Biol. 2: 161-170 [1982]); and 1.5 μl of purified reverse transcriptase. The reaction was incubated at 37° for one hour and then quenched by addition of 1 μl 0.5M EDTA. After addition of 3 μl of 80% glycerol (bromophenol blue and xylene cyanol added as tracers), the reaction mixture was applied to the submerged bed of a 0.7×7 cm column of Bio Gel A50M in 1 mM Tris.Cl, 10 μM EDTA, pH 7.5. The column was eluted in 4-drop (~80 μl) fractions. The first 5 or 6 fractions of the excluded material were pooled and lyophilized overnight in a siliconized eppendorf tube.

The lyophilized cDNA/RNA hybrid was dissolved in 18 μl H$_2$O. To this was added 2.4 μl 10X cacodylkate buffer (1.5M Na-cacodylate, 300 mM Tris.Cl, pH 6.8), 0.6 μl 100 mM CoCl$_2$; 0.6 μl 10 mM dGTP, 14 μCi of α-$^{32}$p-dGTP, and 1 μl (20 units ) of terminal deoxynucleotidyl transferase. After a 30 minute incubation at 37°, the reaction was stopped by addition of 0.5 μl 0.1M EDTA, 0.5 μl 0.5 mg/ml DNAse-free RNAse A, and 19 μl of 10 mM Tris.Cl, 0.5 mM EDTA, pH 7.5 (TE). The mixture was heated to 70° for 5 minutes, then after addition of 0.5 μl 1 mg/ml oligo(dC)$_{12-18}$, to 90° for one minute, and the tube was placed on ice. Second-strand synthesis was accomplished by addition of 0.7 μl 1M MgCl$_2$, 1.0 μl of 5 mM dNTPs, 23 μCi of α-$^{32}$P-dCTP, and 0.5 μl (2.5 units) of DNA polymerase I large fragment. The reaction was incubated at 15° C. for 2 hours, then at 30° for 20 minutes. A 0.5 μl (2.5 units) aliquot of T4 DNA polymerase (Amersham) was added, and the reaction continued at 37° for 30 minutes. The reaction was stopped by addition of of 1 μl 0.5M EDTA, followed by heating at 70° C. for 10 minutes. Internal EcoRI sites in the double-stranded cDNA were methylated by addition of 1.0 μl of 1 mM S-adenosylmethionine and 1 μl (20 units) of EcoRI methylase, followed by incubation at 37° C. for 30 minutes. The reaction was extracted once with 1:1 phenol/CHCl$_3$ and once with CHCl$_3$. Residual CHCl$_3$ was removed by evaporation at 37° C. for 10 minutes, 5 μl of 80% glycerol/dye solution added, and the material was applied to the submerged bed of a BioGel A50M column as before. The first six excluded fractions were pooled and lyophilized overnight as before.

The dry cDNA (about 2 pmol) was dissolved in 15 μl of a solution of phosphorylated EcoRI linkers (75 pmol). This suspension was brought to 19 μl by addition of stock solutions of ATP, DTT, and concentrated ligase buffer. The ligation was started by addition of 1.0 μl of T4 DNA ligase (1 unit) and continued at room temperature for 2 hours. After a 10 minute incubation at 70° C. the reaction was supplemented with 13 μl H$_2$O, 2 μl 0.6M NaCl, 2 μl 10X EcoRI buffer, and 3 μl (30 units) EcoRI. The digestion was continued overnight at 37° C., and quenched by addition of 1 μl 0.5M EDTA, followed by a 70° C., 10 minute incubation. A 5 μl aliquot of glycerol/dye was added, and the material applied to a BioGel A50M column as before. The first five excluded fractions were pooled and lyophilized. The dry cDNA was dissolved in 10 μl TE and stored at 4° C.

A 1 μl aliquot of cDNA was allowed to ligate to 1 μg of EcoRI-cleaved μgt10 DNA in a volume of 5 μl (0.01 unit T4 DNA ligase) at room temperature for 2 hours. This ligation mixture was used directly in an in vitro packing reaction (Amersham). The in vitro packaged DNA was titered on E. coli strains LE392 and C600 hflA to determine the numbers of total phage and phage with cDNA inserts, respectively. Phage bearing cDNA inserts ranged from 2-8% of total phage. An amplified library phage stock was prepared by plating the packaging reaction on C600 hflA (1-2×10$^5$ pfu/150 mm plate). Approximately 10$^6$ independent cDNA clones/μg poly-(A)+RNA were obtained by these procedures, with cDNA insert sizes up to 6 kb.

2. pcD cDNA Library (a) Preparation of vector primer and oligo dG-tailed linker DNAs: The procedure of Okayama, H. and Berg, P. (Mol. and Cell. Biol. 2: 161-170 [1982]) was used with only minor modifications and adapted to the pcDV1 and pL1 plasmids described by Okayama, H. and Berg, P. (Mol. and Cell. Biol. 3: 280-289 [1983]).

An 80 μg sample of pcDV1 DNA was digested at 30° C. with 20 U of KpnI endonuclease in a reaction mixture of 450 μl containing 6 mM Tris-hydrochloride (pH 7.5), 6 mM MgCl$_2$, 6 mM NaCl, 6 mM 2-mercaptoethanol, and 0.1 mg of bovine serum albumin (BSA) per ml. After 16 h the digestion was terminated with 40 μl of 0.25 8.0) and 20 μl of 10% sodium dodecyl sulfate (SDS); the DNA was recovered after extraction with water-saturated 1:1 phenol-CHCl$_3$ (hereafter referred to as phenol-CHCl$_3$) and ethanol precipitation. Homopolymer tails averaging 60, but not more than 80, deoxythymidylate (dT) residues per end were added to the KpnI endonuclease-generated termini with calf thymus terminal deoxynucleotidyl transferase as follows. The reaction mixture (38 μl) contained 140 mM sodium cacodylate-30 mM Tris-hydrochloride (pH 6.8) as buffer, with 1 mM CoCl$_2$, 0.1 mM dithiothreitol, 0.25 mM dTTP, the KpnI endonuclease-digested DNA, and 68 U of the terminal deoxynucleotidyl transferase (P-L Biochemicals, Inc., Milwaukee, Wis.). After 30 min. at 37° C. the reaction was stopped with 20 μl of 0.25M EDTA (pH 8.0) and 10 μl of 10% SDS, and the DNA was recovered after several extractions with phenol-CHCl$_3$ by ethanol precipitation. The DNA was then digested with 15 U of EcoRI endonuclease in 50 μl containing 50 mM NaCl, 10 mM Tris-hydrochloride (pH 7.4), 10 mM MgCl$_2$, 1 mM dithiothreitol, and 0.1 mg of BSA per ml of 5 h at 37° C. The large fragment containing the SV40 polyadenylation site and the pBR322 origin of replication and amplicillin resistance gene was purified by agarose (1%) gel electrophoresis and recovered from the gel by a modification of the glass powder method (Vogelstein, B. & Gillespie, D. Proc. Nat. Acad. Aci. USA 76: 615–619 [1979]). The dT-tailed DNA was further purified by adsorption and elution from an oligo (dA)-cellulose column as follows. The DNA was dissolved in 1 ml of 10 mM Tris-hydrochloride (pH 7.3) buffer containing 1 mM EDTA and 1M NaCl, cooled at 0° C., and applied to an oligo (dA)-cellulose column (0.6 by 2.5 cm) equilibrated with the same buffer at 0° C. The column was washed with the same buffer at 0° C. and eluted with water at room temperature. The eluted DNA was precipitated with ethanol and dissolved in 10 mM Tris-hydrochloride (pH 7.3) with 1 mM EDTA.

The oligo (dG) tailed linker DNA was prepared by digesting 75 μg of pL1 DNA with 20 U of PstI endonuclease in 450 μl containing 6 mM Tris-hydrochloride (pH 7.4), 6 mM $MgCl_2$, 6 mM 2-mercaptoethanol, 50 mM NaCl, and 0.1 mg of BSA per ml. After 16 h at 30° C. the reaction mixture was extracted with phenol-$CHCl_3$ and the DNA was precipitated with alcohol. Tails of 10 to 15 deoxyguanylate (dG) residues were then added per end with 46 U of terminal deoxynucleotidyl transferase in the same reaction mixture (38 μl) described above, except for 0.1 mM dGTP replacing dTTP. After 20 min. at 37° C. the mixture was extracted with phenol-$CHCl_3$, and after the DNA was precipitated with ethanol it was digested with 35 U of HindIII endonuclease in 50 μl containing 20 mM Tris-hydrochloride (pH 7.4), 7 mM $MgCl_2$, 60 mM NaCl, and 0.1 mg of BSA at 37° C. for 4 h. The small oligo (dG)-tailed linker DNA was purified by agarose gel (1.8%) electrophoresis and recovered as described above.

(b) cDNA Library Preparation

Step 1: cDNA synthesis. The reaction mixture (10 μl) contained 50 mM Tris-hydrochloride (pH 8.3), 8 mM $MgCl_2$, 30 mM KCl, 0.3 mM dithiothreitol, 2 mM each dATP, dTTP, dGTP, and dCTP, 20 μCi $\alpha$-$^{32}$P-dCTP(3000 Ci/mmole), 5 μg polyA+ RNA from IgE-induced 23B6 cells, 2 μg of the vector-primer DNA (1.1 pmol of primer end), and 45 U of reverse transcriptase. The reaction was incubated 60 min at 52° C., then stopped by the addition of 1 μl of 0.25M EDTA (pH 8.0) and 0.5 μl of 10% SDS; 40 μl of phenol-$CHCl_3$ was added, and the solution was blended vigorously in a Vortex mixer and then centrifuged. After adding 40 μl of 4M ammonium acetate and 160 μl of ethanol to the aqueous phase, the solution was chilled with dry ice for 15 min., warmed to room temperature with gentle shaking to dissolve unreacted deoxynucleoside triphosphates that had precipitated during chilling, and centrifuged for 10 min. in an Eppendorf microfuge. The pellet was dissolved in 10 μl of 10 mM Tris-hydrochloride (pH 7.3) an 1 mM EDTA, mixed with 10 μl of 4M ammonium acetate, and reprecipitated with 40 μl of ethanol, a procedure which removes more than 99% of unreacted deoxynucleoside triphosphates. The pellet was rinsed with ethanol.

Step 2: Oligodeoxycytidylate [oligo (dC)] addition. The pellet containing the plasmid-cDNA:mRNA was dissolved in 20 μl of 140 mM sodium cacodylate-30 mM Tris-hydrochloride (pH 6.8) buffer containing 1 mM $CoCl_2$, 0.1 mM dithiothreitol, 0.2 μg of poly(A), 70 μM dCTP, 5 μCi $^{32}$p-dCTP, 3000 Ci/mmole, and 60 U of terminal deoxynucleotidyl transferase. The reaction was carried out at 37° C. for 5 min. to permit the addition of 10 to 15 residues of dCMP per end and then terminated with 2 μl of 0.25M EDTA (pH 8.0) and 1 μl of 10% SDS. After extraction with 20 μl of phenol-$CHCl_3$, the aqueous phase was mixed with 20 μl of 4M ammonium acetate, the DNA was precipitated and reprecipitated with 80 μl of ethanol, and the final pellet was rinsed with ethanol.

Step 3: HindIII endonuclease digestion. The pellet was dissolved in 30 μl of buffer containing 20 mM Tris-hydrochloride (pH 7.4), 7 mM $MgCl_2$, 60 mM NaCl, and 0.1 mg of BSA per ml and then digested with 10 U of HindIII endonuclease for 2 h at 37° C. The reaction was terminated with 3 μl of 0.25M EDTA (pH 8.0) and 1.5 μl of 10% SDS, and , after extraction with phenol-$CHCl_3$ followed by the addition of 30 μl of 4M ammonium acetate, the DNA was precipitated with 120 μl of ethanol. The pellet was rinsed with ethanol and then dissolved in 10 μl of 10 mM Tris-hydrochlioride (pH 7.3) and 1 mM EDTA, and 3 μl of ethanol was added to prevent freezing during storage at −20° C.

Step 4: Cyclization mediated by the oligo (dG)-tailed linker DNA. A 9 μl sample of the HindIII endonuclease-digested oligo (dC)-tailed cDNA:mRNA plasmid (90% of the sample) was incubated in a mixture (90 μl) containing 10 mM W Tris-hydrochloride (pH 7.5), 1 mM EDTA, 0.1M NaCl, and 1.8 pmol of the oligo (dG)-tailed linker DNA at 65° C. for 5 min, shifted to 42° C. for 60 min, and then cooled to 0° C. The mixture (90 μl) was adjusted to a volume of 900 μl containing 20 mM Tris-hydrochloride (pH 7.5), 4 mM $MgCl_2$, 10 mM $(NH_4)_2SO_4$, 0.1M KCl, 50 μg of BSA per ml, and 0.1 mM β-NAD; 6 μg of E. coli DNA ligase, and the solution was then incubated overnight at 12° C.

Step 5: replacement of RNA strand by DNA. To replace the RNA strand of the insert, the ligation mixture was adjusted to contain 40 μM of each of the four deoxynucleoside triphosphates, 0.15 mM β-NAD, 4 μg of additional E. coli DNA ligase, 16 U of E. coli DNA polymerase I, and 9 U of E. coli RNase H. This mixture (960 μl) was incubated successively at 12° C. and room temperature for 1 h each to promote optimal repair synthesis and nick translation by DNA polymerase I.

Step 6: Transformation of E. coli. Transformation was carried out using minor modifications of the procedure described by Cohen et al. (Proc. Nat. Acad. Sci. USA, 69: 2110–2114 [1972]). E. coli K-12 strain MC1061 (Casadaban, M. and Cohen, S., J. Mol. biol. 138: 179–207 [1980]) was grown to 0.5 absorbancy unit at 600 nm at 37° C. in 20 ml of L-broth. The cells were collected by centrifugation, suspended in 10 lm of 10 mM Tris-hydrochloride (pH 7.3) containing 50 mM $CaCl_2$, and centrifuged at 0° C. for 5 min. The cells were resuspended in 2 ml of the above buffer and incubated again at 0° C. for 5 min.; then, 0.2 ml of the cell suspensions was mixed with 0.1 ml of the DNA solution (step 5) and incubated at 0° C. for 15 min. After the cells were kept at 37° C. for 2 min. and therafter at room temperature for 10 min., 0.5 ml of L-broth was added, and the culture was incubated at 37° C. for 30 min., mixed with 2.5 ml of L-broth soft agar at 42° C., and spread over L-broth agar containing 50 μg of ampicillin per ml. After incubation at 37° for about 12 hr, the colonies were scraped from the plates into L-broth. This bacterial suspension was used to inoculate 1 liter of L-broth containing 50 μg/ml amplicillin. After about 8 hr at 37° with shaking, aliquots of the culture were brought to 7% DMSO and stored at -70° C. Approximately $1 \times 10^5$ independent cDNA clones were generated by this procedure.

F. Preparation of Subtracted cDNA probe (1) $^{32}$P-cDNA synthesis:

5 μg of polyA+ mRNA from IgE-induced 23B6 cells in 3 μl of H$_2$O was heated for 5 min at 65° C:, then added to a reaction containing 50 mM Tris-Cl pH 8.3, 8 mM MgCl$_2$, 30 mM KCl, 0.7 mM DTT, 1 mM each of dATP, dGTP, dTTP, 50 μM dCTP, 10 μg/ml oligo (dT)$_{12-18}$ (Collaborative Research), 100 μg/ml Actinomycin D, 500 μCi α$^{32}$P-dCTP (3000 Ci/mmole; Amersham) and 150 units reverse transcriptase (Life Sciences, Inc., St. Petersburg, Fla. in a total volume of 100 μl. Following a 2 hr incubation at 40° C., 0.5 μl of the reaction was removed for precipitation in trichloroacetic acid to determine the amount of $^{32}$p incorporated. Then, 100 μl of 0.2 N NaOH was added, and the sample was heated 20 min at 70° C. to hydrolyze the RNA. After cooling, the reaction was neutralized was 20 μl of 1 N HCl and 4 μl of 1 mg/ml tRNA was added as carrier. The sample was extracted twice with an equal volume of phenol-chloroform (1:1). It was then precipitated with an equal volume of 4M ammonium acetate and 2 volumes of ethanol. The pellet was resuspended in 100 μl H$_2$O, the precipitation repeated, and the pellet washed twice with 80% ethanol.

(2) Subtractive hybridization:

$^{32}$P-cDNA (synthesized as described above) was co-precipitated with 50 μg of polyA+ mRNA from BW5147. The pellet was resuspended in 7 μl H$_2$O, 1 μl 4M Na phosphate, pH7, 0.1 μl 20% SDS, and 0.1 μl 1 0.1M EDTA, then the entire sample was sealed in a capillary tube. The sample was heated 5 min at 90° C., then shifted to 68° C. for 14 hrs. (Cot $\geq$ 5000). The hybridization mixture was then diluted to 1 ml with 0.12M sodium phosphate pH 7.0, 0.1% SDS, and the temperature of the mixture raised to 60° C. This was loaded on a column of 0.4 gm hydroxylapatite equilibrated in the same buffer and kept at 60° C. The flow-through was collected and the column was then washed with 5 ml of the same buffer at 60° C. 1 ml fractions were collected and 1 μl aliquots of each fraction were counted in a scintillation counter. The peak of single stranded cDNA in fractions 2, 3, and 4 was pooled. This material, representing 11% of the mass of the starting $^{32}$P-cDNA, was concentrated to 0.3 ml by repeated extraction with n-butanol, then used as a hybridization probe.

G. Hybrid Selections (1) Preparation of plasmids containing cDNA clone fragments.

Hybrid selections were performed with plasmid cDNA preparations isolated as follows. 4×10$^4$ random cDNA clones from the λgt10 cDNA library were screened with the subtracted cDNA probe. 270 hybridizing μgt10 cDNA clones were picked and pooled. DNA was prepared (Maniatis, T. et al., ""Molecular Cloning," Cold Spring Harbor, pp. 76–85 [1982]) from this pool of λ phage clones and 30 μg of this DNA was digested to completion with EcoRI. The cDNA insert EcorRI fragments were purified by agarose (1%) gel electrophoresis and recloned into EcoRI-cleaved, dephosphorylated pUC8 (PL-Biochemicals; Vierira, H. and Messing, L. Gene 19: 259–268 [1982]). Approximately 700 transformants were again screened with the subtracted $^{32}$P-cDNA probe and 912 hybridizing colonies were picked individually by sterilized toothpicks. Plasmid preparations were prepared from individual colonies and from pools thereof (Maniatis, T. op. cit., 86–95) for use in hybrid-selection experiments.

(2) Preparation of DNA filters

All plasmid DNAs were linearized by digestion with BamHI prior to binding to nitrocellulose filters. Digestions were performed in 50 μl containing: 10 mM Tris.Cl pH 7.9, 10 mM MgCl$_2$, 10 μg plasmid DNA, 50 mM NaCl, and 10 units BamHI. Following a 2 hr incubation at 37° C., samples were diluted to 200 μl with TE (10 mM Tris.Cl pH 8.0, 1 mM EDTA) and extracted with an equal volume (200 μl) of phenol saturated with TE. 20μl of 3M sodium acetate, pH 6, was added to the aqueous phase, and DNA was precipitated with 2 volumes of ethanol. The DNA pellets were recovered by centrifugation, then washed with 70% ethanol. The dried pellet was resuspended in 150μl of sterile H$_2$0 for each 10μg of DNA. Duplicate filters were prepared for each DNA sample, 10μg DNA per filter. The DNA in 150μl of H$_2$0 was boiled for 10 min. then 150μl 1N NaOH was added and the solution incubated 20 min at room temperature. The sample was chilled on ice, then 150μl 1M HCl, 1M NaCl, 0.3M Na-citrate and 0.5M Tris-Cl pH 8.0 was added.

0.9cm Millipore HAWP filters wet with distilled H$_2$O were fitted into a micro-filtration apparatus (Schleicher and Schuell). The denatured and neutralized DNA solution from above was filtered through by centrifugation at 500 rpm for 5 min. Filters were washed with 1ml of 6XSSC, then air dried before baking 2 hrs. at 80° C.

(3) RNA/DNA Hybridizations

Hybridizations were performed in 200 μl containing 65% (v/v) redistilled formamide, 20 mM PIPES, pH 6.4, 0.4M NaCl, 100 μg/ml calf liver tRNA, 100 μg/ml polyA+ mRNA from IgE-induced 23B6. Each hybridization solution was heated for 3 min at 70° C., then two DNA filters (10 μg DNA/filter) were cut into quarters and added to the solution. Hybrids were incubated at 50° for 4 hours followed by 4 hour incubations at 46° C. and 42° C. After this period the supernatants were removed and the filters washed 3 times with 1 ml of: 10mM Tris.Cl pH 7.4, 0.15M NaCl, 1 mM EDTA, 0.5% SDS. This was followed by three 1ml washes with the same buffer lacking SDS. Both buffers were kept at 65° for the washes. To elute the hybridized mRNA, 400 μl of H$_2$O with 5 μg calf liver tRNA was added to the vial with the filters. The tubes were boiled for 3 min, then quick chilled in dry ice/ethanol. Samples were then thawed, and the eluted RNA precipitated with 2 volumes of ehtanol and 1/10 volume 3M Na acetate, pH 6. RNA pellets were collected by centrifugation and washed twice with 70% ethanol. The dried pellets were resuspended in 2μl of oocyte injection buffer and the entire sample was injected into oocytes (see above).

Supernatants from oocytes injected with RNA selected with the pool of 192 clones inhibited 33% of IgE-specific rosettes, while in the same experiment, supernatants from oocytes injected with the unselected, IgE-induced cell RNA inhibited 23% of IgE-specific rosettes. An unrelated plasmid (a cDNA encoding rat IgE-heavy chain in this case, but pBR322 would suffice) was also used in a hybrid-selection as a negative control; only a background level of rosette inhibition was obtained.

Pooled and individual pUC8 clones were examined by hybrid-selection and in vitro translation as described above. Five clones were identified, based on their activity in this assay, as cDNA fragments which share homology with mRNAs encoding IgE-binding factors.

The sizes of these cDNA inserts ranged from 300 bp (base pairs) to 1200 bp (Table II).

TABLE II

Hybrid-Selection and In Vitro Translation of IgE-Binding Factor Activity in Xenopus Oocytes[a]

| cDNA on filter[b] | IgE-specific rosette inhibition, %[c] |
| --- | --- |
| Experiment 1 (not selected) | 23% |
| rat IgE cDNA (1400 bp) | 6% |
| pool of 192 pUC8 clones | 33% |
| Experiment 2 (not selected) | 30% |
| A18 (1200 bp) | 35% |
| 6 (300 bp) | 32% |
| 55 (350 bp) | 19% |
| 104 (575 bp) | 28% |
| 112 (420 bp) | 23% |

[a]RNA used in these experiments was isolated from "induced" 23B6 cells which were cultured with IgE.
[b]cDNA fragment insert size in parentheses.
[c]Average of at least two determinations.

H. Screening of pcD cDNA Library and DNA Transfections

The 1200 bp EcoRI fragment of A18 (Table II) was purified by 1% agarose gel electrophoresis. This purified fragment was radiolabeled by nick-translation using DNA polymerase I and $\alpha$-$^{32}$P-dCTP. This $^{32}$P-DNA probe was used to screen approximately $10^5$ clones of the pcD cDNA library. 104 clones which hybridized to this probe were picked. Plasmid DNA was prepared from each of these clones as described earlier.

One day prior to transfection, approximatley $10^6$ Cos7 monkey cells were seeded onto individual 100 mm plates in DME containing 10% fetal calf serum an 2 mM glutamine. To perform the transfection, the medium was aspirated from each plate and replaced with 4.0 ml of DME containing 50 mM Tris.HCl, pH 7.4, 400 $\mu$g/ml DEAE-Dextran and 50 $\mu$g of the plasmid DNAs to be tested. The plates were incubated for four hours at 37° C., then the DNA-containing medium was removed, and the plates were washed twice with 5 ml of serum-free DME. 7.0 ml of DME containing 4% fetal calf serum and 2 mM glutamine was added to the plates which were then incubated 72 hours at 37° C. The growth medium was collected and assayed for IgE-binding factor activity as described above.

Assay of supernatants from transfection experiments with 70 of these cDNA clones yielded eight cDNAs capable of directing synthesis in Cos7 cells of secreted factors which inhibit IgE-specific rosette formation (Table III). Supernatants from transient expression experiments with four of these clones (designated 23B6p4.2, 23B6p8.3, 23B6p9.5, and 23B6p10.2; and designated by ATCC accession numbers 39632, 39633, 39634, 39635, respectively) were selected for further characterization. The IgE-binding factors present in these supernatants all bound specifically to IgE-coupled Sepharose, and could be eluted at acid pH (Table IV).

The IgE-binding factors in IgE-Sepharose eluates (Table IV) derived from transient expression experiments with the four clones were tested for the ability to selectively suppress or potentiate an IgE response by antigen-primed rat lymphocytes in vitro, as described above in detail. Generally, the affinity-purified IgE-binding factors were added to cultures of antigen-stimulated rat mesenteric lymph node cells, and after five days in culture IgE- and IgG-containing cells were enumerated by immunofluorescence. The results of these experiments are shown in FIG. 2. IgE-binding factors from transient expression experiments with cDNA clones 23B6p8.3 and 23B6p9.5 enhanced the number of IgE-containing cells in these cultures approximately four-fold. Similar results were obtained with a preparation of IgE-potentiating factor derived from lymphocytes from a rat infected with the parasite *Nippostrongylus brasiliensis* (Suemura, M. and Ishizaka, K. J. Immunol. 123: 918-924 [1979]; Suemura, M. et al., J. Immunol. 125: 148-154 [1980]. In contrast, IgE-binding factors from transfections with cDNA clones 23B6p4.2 and 23B6p10.2 exhibited neither IgE-suppressive nor IgE-potentiating factor activity in vitro. In all experiments, the IgG response remained unaffected, thus illustrating that the observed potentiating activity is specific for the IgE response.

TABLE III

Transient Expression of IgE-Binding Factors in Cos7 Monkey Kidney Cells

| cDNA Clone | Inhibition of IgE-specific rosettes, % |
| --- | --- |
| 4.2 | 24 |
| 8.3 | 36 |
| 8.6 | 35 |
| 9.5 | 20 |
| 10.2 | 33 |
| 10.8 | 41 |
| 11.7 | 18 |
| 17.5 | 24 |

TABLE IV

IgE-Binding Factors in Cos7 Cell Transfection Supernatants Bind to IgE-Sepharose[a]

| cDNA Clone | Supernatant | Inhibition of IgE-specific Rosettes, % | |
| --- | --- | --- | --- |
| | | IgE-Sepharose effluent | eluate |
| 4.2 | 24 | 0 | 25 |
| 8.3 | 36 | 0 | 31 |
| 9.5 | 20 | 0 | 24 |
| 10.2 | 33 | 3 | 21 |

[a]The elution of the IgE-sepharose column results in a 1:4 dilution of the original material. Therefore, the "supernatant" value was obtained from a 1:4 dilution of the material applied to the immunosorbent.

Figure 3:
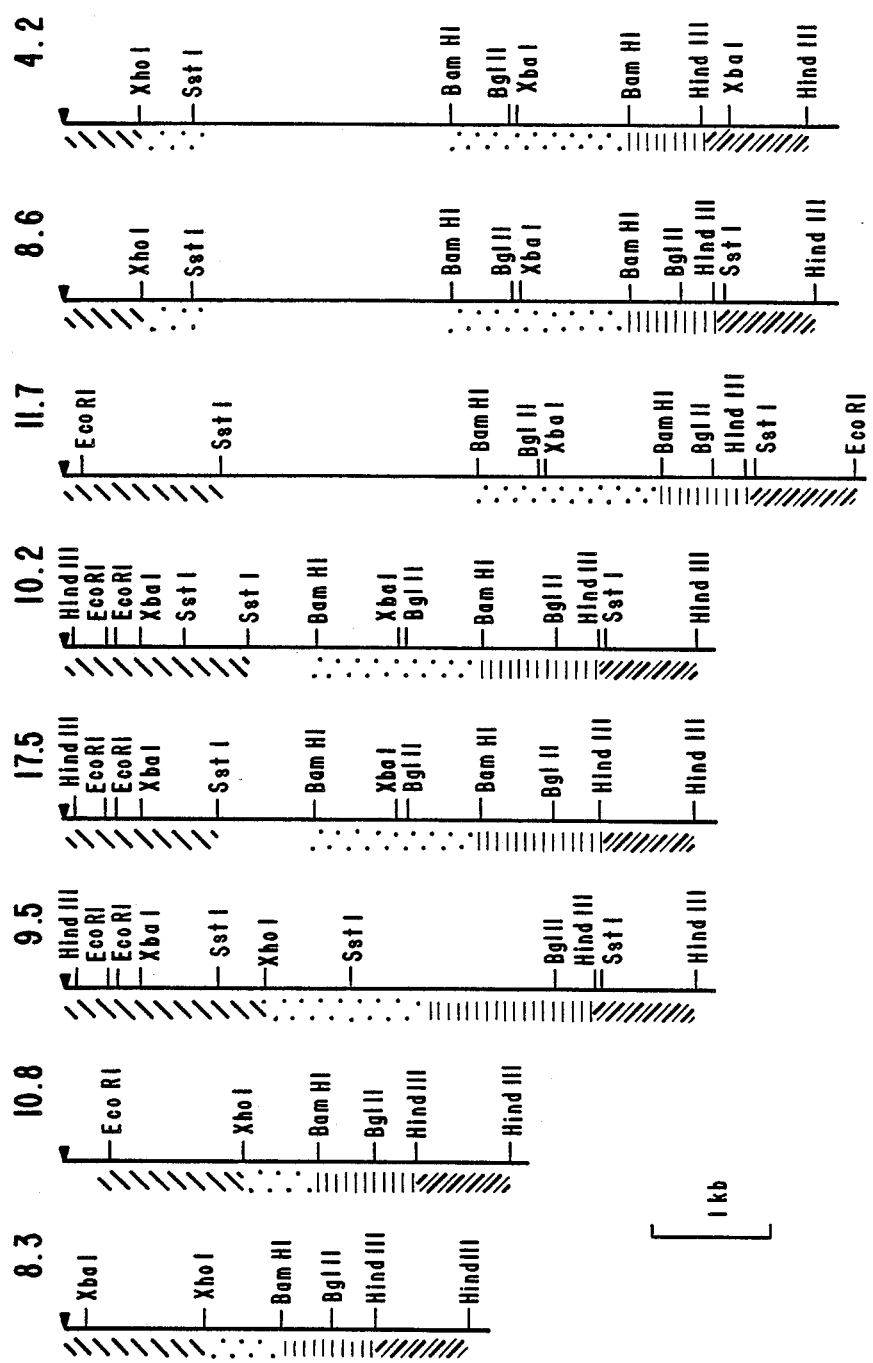
FIG. 3 is an illustration of restriction endonuclease cleavage maps of eight cDNAs of the present invention.

The experimentally determined complete sequence of cDNA clone 23B6p8.3, which directs expression of IgE-potentiating factor activity in Cos7 cells, is shown in FIG. 1. This cDNA contains an open reading frame consisting of 556 codons beginning with the methionine codon at position 94. This open reading frame encodes the putative amino acid sequence shown in FIG. 1. It is recognized that the IgE-binding factor defined by this translated sequence is a precursor protein which may be subject to further cellular modifications, such as by glycosylation and by proteolysis after translation. The restriction endonuclease cleavage maps of 23B6p8.3 and seven other cDNA inserts are shown in FIG. 3.

Figure 4:
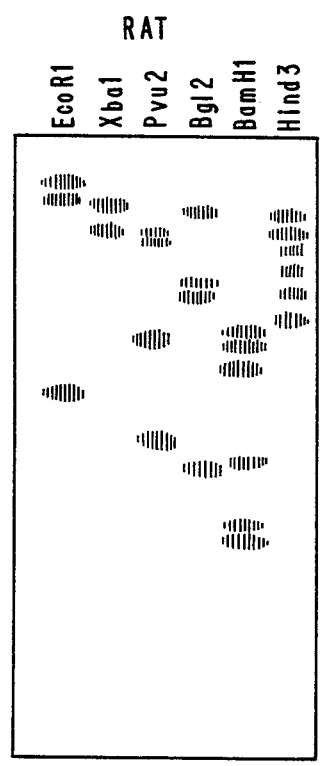
FIG. 4 shows the hybridization pattern of IgE binding factor cDNA probes to restriction digests of rate genomic DNAs.

FIG. 4 shows hybridization of a 600 bp XhoI/Bam HI fragment from clone 23B6p8.3 to restriction digests of rat sperm genomic DNA. This probe, which contains a substantial portion of the coding sequence, hybridizes to multiple restriction fragments, as can be seen in FIG. 4. This result suggests that this clone may be homologous to a family of similar, but distinct genes in the rat genome. Thus, IgE-binding factor genes may be members of a small multigene family. The other members of this gene family could encode molecules with similar functions, i.e., immunoglobulin binding fators which regulate expression of the other immunoglobulin chains (Lowy, I., et al., Proc. Nat. Acad. Sci. USA 80: 2323-2327 [1983]; Yodoi, J., et al., J. Immunol. 131: 303-310 [1983]). Often, a few individual genes in these multigene families are found to be pseudogenes incapable of encoding functional proteins, for examples Steinmetz, M., et al. (Cell 25: 683-692 [1981]), and Hollis, G., et al. (Nature 296: 321-325 [1982]). However, most members of a multigene family usually encode functional, related proteins.

From the foregoing, it will be appreciated that the cDNA clones of the present invention provide accurate and complete sequence data on mammalian IgE binding factors. The invention provides those skilled in the art means for producing significant quantities of these factors.

Although the invention has been described in some detail by way of illustration and example, it will also be apparent that various changes and modifications can be made without departing from the scope and spirit of the appended claims.

On Mar. 15, 1984, Applicants deposited with the American Type Culture Collection, Rockville, Md., USA (ATCC), the hybridoma 23B6 under the ATCC accession number HB2581, and the vectors 23B6p4.2, 23B6p8.3, 23B6p9.5, and 23B5p10.2, under ATCC accession numbers 39632, 39633, 39634, and 39635, respectively.

This deposit was made under conditions as provided under ATCC's agreement for Culture Deposit for Patent Purposes, which assures that this deposit will be made available to the U.S. Commissioner of Patents and Trademarks pursuant to 35 USC 122 and 37 CFR 1.14, and will be made available to the public upon issue of a U.S. patent which requires this deposit to be maintained. Availability of the deposited strain is not to be construed as a license to practice the invention in contravention of the rights granted under the authority of any government in accordance with its patent laws.

We claim:

1. A process for producing a polypeptide exhibiting mammalian IgE binding factor activity; said process comprising the steps of:
    providing a vector comprising a nucleotide sequence coding for said polypeptide, wherein the nucleotide sequence is capable of being expresed by a host containing the vector and wherein the nucleotide sequence is the complementary DNA insert of a vector selected from the group consisting of 23B6p4.2, 23B56p8.3, 23B6p9.5, and 23B6p10.2;
    incorporating the vector into the host; and
    maintaining the vector-containing host under conditions suitable for expression of the nucleotide sequence into said polypeptide.

2. The process of claim 1 wherein the host is an organism transformed or transfected with the vector.

3. The process of claim 2 wherein the host is a eukaryotic cell.

4. The process of claim 1 wherein the vector comprises the nucleotide coding for said polypeptide linked to a second nucleotide sequence, wherein the second nucleotide sequence is capable of controlling expression of the nucleotide sequence coding for said polypeptide.

5. The process of claim 4 wherein the second nucleotide sequence comprises a promoter sequence which promotes express of the nucleotide sequence coding for said polypeptide.

6. The process of claim 4 wherein the host is a mammalian cell.

7. The process of claim 6 wherein the second nucleotide sequence comprises a promoter sequence, one or more intron sequences, an da polyadenylation sequence, whereby the nucleotide sequence coding for said polypeptide is transcribed, spliced and polyadenylated prior to translation in the mammalian cell.

8. The process of claim 7 wherein the promoter sequence is an SV40 virus early region promoter and the polyadenylation sequence is an SV40 virus late region polyadenylation sequence.

9. The process of claim 8 wherein the mammalian cell is a monkey Cos7 cell.

10. The process of claim 1 wherein said polypeptide includes a leader sequence.

11. The process of claim 1 wherein said host is a mammalian cell, and wherein said polypeptide is glycosylated and exhibits either IgE potentiating factor activity of IgE suppressive factor activity.

12. The process of claim 11 wherein said mammalian cell is selected so that said polypeptide exhibits IgE suppressive factor activity.

13. The process of claim 11 wherein said mammalian cell is selected so that said polypeptide exhibits IgE potentiating factor activity.

14. A replicable vector carrying a DNA sequence encoding for a polypeptide exhibiting IgE binding factor activity, said vector being selected from the group consisting of 23B6p4.2, 23B6p8.3, 23B6p9.5, and 23B6p10.2.

15. A nucleic acid selected from the group consisting of the inserts of vector 23B6p4.2, 23B6p8.3, 23B6p9.5, or 23B6p10.2.

16. A mammalian nucleic acid capable of encoding a polypeptide exhibiting IgE binding factor activity, the mammalian nucleic acid having a nucleotide sequence selected from the group consisting of:

GCT—TTA—CAA—GTT—ATG—TTT—GGC—CTT—

10
GAA—TTT—TTT—CTA—GTG—TTA—GAA—GCC—

20
CTT—TTG—TTC—CTT—TTC—ACA—TGT—TAT—

30
CAA—GTG—GTT—AAG—GCA—GGG—CGG—ATT—

40
CTA—GAT—GAA—ATT—CAG—GAC—AAG—CTA—

TCA—GAA—GTA—AAG—CGG—GGA—GAG—AGA—

50
GTA—GGA—ACA—AAG—AGG—AAA—TAT—GGT—

60
ACA—CAA—AAT—AAG—TAT—ACA—GGC—CTT—

70
TCC—AAG—GGT—CTT—GAA—CCC—GAG—GAA—

80
AAG—TTA—AGG—TTA—GGT—AGG—AAT—ACC—

TGG—AGA—GAG—ATT—AGA—AGA—AAA—AGA—

90
GGA—AAA—AGG—GAA—AAG—AAG—AAA—GAT—

100
CAA—TTA—GCG—GAG—GTC—TCT—AGG—AAA—

-continued

```
                     110
AGG—AGC—CTG—TGC—TCA—TCG—CTG—GAT—
                     120
GGG—CTC—GGG—AAG—CCA—GCT—CTT—AGT—
AGC—TCT—GAA—GCA—GGT—GAA—GAA—TCC—
             130
TCC—TCT—GAG—GAA—ACA—GAC—TGG—GAG—
                     140
GAA—GAA—GCA—GCC—CAT—TAC—CAG—CCA—
                     150
GCT—AAT—TGG—TCA—AGA—AAA—AAG—CCA—
                         160
AAA—GCG—GCT—GGC—GAA—GGC—CAG—TTT—
GCT—GAT—TGG—CCT—CAG—GGC—AGT—CGG—
         170
CTT—CAA—GGT—CCG—CCC—TAT—GCG—GAG—
                 180
TCC—CCG—CCC—TGC—GTA—GTG—CGT—CAG—
                 190
CAA—TGC—GCA—GAG—AGA—TGC—GCA—GAG—
                             200
AGG—CAG—TGC—GCA—GAG—AGG—CAG—TGC—
GCA—GAC—TCA—TTC—ATT—CCC—AGA—GAG—
     210
GAA—CAA—AGG—AAA—ATA—CAA—CAG—GCA—
             220
TTT—CCG—GTC—TTT—GAA—GGA—GCC—GAG—
                     230
GGT—GGG—CGT—GTC—CAC—GCT—CCG—GTA—
                         240
GAA—TAC—TTA—CAA—ATT—AAA—GAA—ATT—
GCC—GAG—TCG—GTT—CGT—AAA—TAT—GGA—
     250
ACC—AAT—GCT—AAT—TTT—ACC—TTG—GTG—
             260
CAG—TTA—GAC—AGG—CTC—GCC—GGC—ATG—
                 270
GCA—CTA—ACT—CCT—GCT—GAC—TGG—CAA—
                         280
ACG—GTT—GTA—AAA—GCC—GCT—CTC—CCT—
AGT—ATG—GGC—AAA—TAT—ATG—GAA—TGG—
     290
AGA—GCG—CTT—TGG—CAC—GAA—GCT—GCA—
             300
CAA—GCG—CAG—GCC—CGA—GCA—AAC—GCA—
                 310
GCT—GCT—TTG—ACT—CCA—GAG—CAG—AGA—
                         320
GAT—TGG—ACT—TTT—GAC—TTG—TTA—ACG—
GGT—CAG—GGA—GCT—TAT—TCT—GCT—GAT—
         330
CAG—ACA—AAC—TAC—CAT—TGG—GGA—GCT—
```

```
                 340
TAT—GCC—CAG—ATT—TCT—TCC—ACG—GCT—
                     350
ATT—AGG—CCT—GGA—AGG—CGC—TCT—CGA—
                     360
GCA—GGT—GAA—ACC—ACT—GGT—CAG—TTA—
ACA—AAG—ATA—ATC—CAG—GGA—CCT—CAG—
                 370
GAA—TCC—TTC—TCA—GAT—TTT—GTG—GCC—
                 380
AGA—ATG—ACA—GAG—GCA—GCA—GAG—CGT—
                     390
ATT—TTT—GGA—GAG—TCA—GAG—CAA—GCT—
                             400
GCG—CCT—CTG—ATA—GAA—CAG—CTA—ATC—
TAT—GAG—CAA—GCC—ACA—AAG—GAG—TGC—
             410
CGA—GCG—CTC—CAT—AGC—CCC—AAG—AAA—
                 420
GAA—CAA—AGG—CTT—ACA—AGA—CTG—GCT—
                     430
CAG—GGT—CTG—TCG—AGA—GCT—TGG—GGG—
                         440
AAA—CCC—AGA—CTC—CTT—AAG—ACT—GAT—
AAT—GGA—CCA—GCT—TAT—ACG—TCT—CAA—
         450
AAA—TTC—CAA—CAG—TTC—TGC—CGT—CAG—
             460
ATG—GAC—GTG—ACC—CAC—CTG—ACT—GGA—
                 470
CTT—CCA—TAC—AAC—CCT—CAA—GGA—CAG—
                         480
GGT—ATT—GTT—GAG—CGT—GCG—CAT—CGC—
ACC—CTC—AAA—GCC—TAT—CTT—ATA—AAA—
         490
CAG—AAG—AGG—GGA—ACT—TTT—GAG—GAG—
                 500
ACT—GTA—CCC—CGA—GCA—CCA—AGA—GTG—
                     510
TCG—GTG—TCT—TTG—GCA—CTC—TTT—ACA—
                         520
CTC—AAT—TTT—TTA—AAT—ATT—GAT—GCT—
CAT—GGC—CAT—ACT—GCG—GCT—GAA—CGT—
         530
CAT—GTT—CAG—AGC—CAG—ATA—GGC—CCA—
                 540
ATG—AGA—TGG—TTA—AAT—GGA—AAA—ATG—
                 550
TCC—TTG—ATA—ATA—AAT—GGT—ATG—GCC—
CGG—ATC—CTA—TCT
AND
GCT—TTA—CCA—GGT—ATG—TTT—GGC—CTT—
```

-continued

```
        10
GAA—CTT—TTT—CTA—GTG—TTA—GGA—GCC—
        20
CTT—TTG—TTC—CTT—TTC—ACA—TGT—TAT—
        30
ATA—GTG—CTT—AAG—GCA—GGG—CTA—AAA—
                    40
ATT—CTA—GAG—GAA—ATT—CAG—GAC—AGT—
CTA—TCA—GAA—GTA—AAG—CGG—AGA—GAG—
        50
AGA—GTA—GGA—ACA—AGG—AGA—AAC—GGT—
            60
AAG—TAT—ACA—GGC—CTT—TCC—AAG—GGT—
        70
CTT—GAA—CCC—GAG—GAA—AAG—TTA—AGG—
                80
TTA—GGT—AGG—AAT—ACC—TGG—AGA—GAG—
ATT—AGA—AGA—AAA—AGA—GGA—AAA—AGG—
    90
GAG—AAG—AAA—AAA—GAT—CGA—TTA—GCG—
        100
GAG—CTC—TCT—AGG—AGA—TAC—TCG—TCA—
            110
CTA—GAT—GAG—CTC—AGG—AAG—CCA—GCT—
                120
CTT—AGT—AGT—TCT—GAA—GCA—GAT—GAA—
GAA—TCC—TCC—TCT—GAG—GAA—ACA—GAC—
    130
TGG—GAG—GAA—GAA—GCA—GCC—CAT—TAC—
        140
CAG—CCA—GCT—AAT—CGG—TCA—AGA—AAA—
            150
AAG—CCA—AAA—GCG—GCT—GGC—GAA—GGG—
                160
CAT—TTG—CTA—ATT—GGC—CTC—AGG—GCA—
ATC—GGC—TAC—CAG—GTG—CAC—TCC—CGC—
    170
CCT—ATG—CGA—GTC—CCG—CCC—TGC—GTA—
            180
GTG—CGT—CAG—CCC—GTA—GTG—CGT—CAG—
        190
CAA—TGC—GCA—GAG—AGG—CAG—TGC—GCA—
                200
GAG—AGG—CAG—TGC—GCA—GAC—TCA—TTC—
ATT—CCC—CGA—GAG—GAA—CAA—AGG—AAA—
    210
ATA—CAA—CAG—GCA—AAA—CCA—GTC—TTT—
        220
GAA—GGA—GCC—GAG—GGT—GGG—CGT—GTC—
            230
CAC—GCT—CCG—GTA—GAA—TAT—GTG—CAG—
                240
ATT—AAA—GAA—ATT—GCC—GAG—TCG—GTC—
```

```
CGT—AAA—TAT—GGA—ATC—AAT—GCT—AAT—
    250
TTT—ACC—TTG—GTG—CAG—TTA—GAC—AGG—
        260
CTT—GCC—AGC—ATG—GCA—CTA—ACT—CCT—
            270
GCC—GAC—TGG—CAA—ATG—ATT—GCA—AAA—
                280
GCC—GCT—CTC—CCT—AGT—ATG—GCC—AAA—
TAT—GTG—GAA—TGG—CGA—GCT—CTG—TGG—
    290
CAG—GAG—GCG—GCA—CAG—GCG—CAG—GAC—
        300
CGA—GCA—AAC—GCT—GCT—GCT—TTA—ACT—
            310
CAA—GAG—CAG—AGA—GAT—TGG—ACT—TTT—
                320
GAC—TTG—TTA—ACG—GGT—CAG—AGA—GCT—
TAT—TCT—GCT—GAA—CCT—GAT—AAG—AGG—
    330
TAT—CAA—TGG—AAG—GTC—TTA—CCA—CAG—
        340
GGA—ATG—TCC—AAT—AGT—CCT—ACA—ATG—
            350
TGC—CAA—CTT—TAT—GTG—CAA—GAA—GCT—
                360
CTT—TTG—CCA—GTG—AGG—AAA—CAG—TTC—
CCC—TCT—TTA—ATT—TTG—CTC—CTT—TAC—
    370
ATG—GAT—GAC—ATC—CTC—CTG—TGC—CAT—
        380
AAA—GAC—CTT—ACC—ATG—CTA—CAA—AAG—
            390
GCA—TAT—CCT—TTT—CTA—CTT—AAA—ACT—
                400
TTA—AGT—CAG—TGG—GGT—CTA—CAG—ATA—
GCC—ACA—GAA—AAG—GTC—CAA—ATT—TCT—
    410
GAT—ACA—GGA—CAA—TTC—TTG—GGC—TCT—
        420
GTG—GTG—TCC—CCA—GAT—AAG—ATT—GTG—
            430
CCC—CAA—AAG—GTA—GAG—ATA—AGA—AGA—
                440
GAT—CAC—CTC—CAT—ACC—TTA—AAT—GAT—
TTT—CAA—AAG—CTG—TTG—GGA—GAT—ATT—
    450
AAT—TGG—CTC—AGA—CCT—TTT—TTA—AAG—
        460
ATT—CCT—TCC—GCT—GAG—TTA—AGG—CCT—
            470
TTG—TTT—AGT—ATT—TTA—GAA—GGA—GAT—
```

-continued

CCT—CAT—ATC—TCC—TCC—CCT—AGG—ACT—
CTT—ACT—CTA—GCT—GCT—AAC—CAG—GCC—
                490
TTA—CAA—AAA—GTG—GAA—AAA—GCC—TTA—
              500
CAG—AAT—GCA—CAA—TTA—CAA—CGT—ATT—
                510
GAG—GAT—TCG—CAG—CCT—TTC—AGT—TTG—
                  520
TGT—GTC—TTT—AAG—ACA—GCA—CAA—TTG—
CCA—ACT—GCA—GTT—TTG—TGG—CAA—AAT—
        530
GGG—CCA—TTG—TTG—TGG—ATC—CAT—CCA—
            540
AAC—GTA—TCC—CCA—GCT—AAA—ATA—ATA—
              550
GAT—TGG—TAT—CCT—GAT—GCA—ATT—GCA—
                560
CAG—CTT—GCC—CTT—AAA—GGC—CTA—AAA—
GCA—GCA—ATC—ACC—CAC—TTT—GGG—CAA—
        570
AGT—CCA—TAT—CTT—TTA—ATT—GTA—CCT—
            580
TAT—ACC—GCT—GCA—CAG—GTT—CAA—ACC—
              590
TTG—GCA—GCC—GCA—TCT—AAT—GAT—TGG—
                600
GCA—GTT—TTA—GTT—ACC—TCC—TTT—TCA—
GGA—AAA—ATA—GAT—AAC—CAT—TAT—CCA—
    610
AAG—CAT—CCA—ATC—TTA—CAG—TTT—GCC—
                620
CAA—AAT—CAA—TCT—GTT—GTG—TTT—CCA—

-continued

CAA—ATA—ACA—GTA—AGA—AAC—CCA—CTT—
                            640
AAA—AAT—GGG—ATT—GTG—GTA—TAT—ACT—
GAT—GGA—TCA—AAA—ACT—GGC—ATA—GGT—
      650
GCC—TAT—GTG—GCT—AAT—GGT—AAA—GTG—
        660
GTA—TCC—AAA—CAA—TAT—AAT—GAA—AAT—
                670
TCA—CCT—CAA—GTG—GTA—GAA—TGT—TTA—
                          680
GTG—GTC—TTA—GAA—GTT—TTA—AAA—ACC—
TTT—TTA—GAA—CCC—CTT—AAT—ATT—GTG—
    690
TCA—GAT—TCC—TGT—TAT—GTG—GTA—AAT—
          700
GCA—GTA—AAT—CTT—TTA—GAA—GTG—GCT—
              710
GGA—GTG—ATT—AAG—CCT—TCC—AGT—AGA—
                    720
GTT—GCC—AAT—ATT—TTT—CAG—CAG—ATA—
CAA—TTA—GTT—TTG—TTA—TCT—AGA—AGA—
      730
TCT—CCT—GTT—TAT—ATT—ACT—CAT—GTT—
              740
AGA—GCC—CAT—TCA—GGC—CTA—CCT—GGC—
                  750
CCC—ATG—GCT—CTG—GGA—AAT—GAT—TTG—
                    760
GCA—GAT—AAG—GCA—CTA—AAG—TGG—TGC—
TGC—TGC—CCT—ATC—ATC—CCC—GGT—AGA—
    770
GGC—TGC—AAG—AAA—TTT—TCA.

* * * * *